United States Patent [19]

Bowie

[11] Patent Number: 5,750,345
[45] Date of Patent: May 12, 1998

[54] DETECTION OF HUMAN α-THALASSEMIA MUTATIONS AND THEIR USE AS PREDICTORS OF BLOOD-RELATED DISORDERS

[75] Inventor: Lemuel J. Bowie, Evanston, Ill.

[73] Assignee: Evanston Hospital Corporation, Evanston, Ill.

[21] Appl. No.: 550,715

[22] Filed: Oct. 31, 1995

[51] Int. Cl.$^6$ .................. C12Q 1/68; C12P 19/34; C07H 21/04

[52] U.S. Cl. .................. 435/6; 435/91.2; 536/24.33; 935/77; 935/78

[58] Field of Search .................. 435/6, 91.2; 935/8, 935/77, 78; 536/23.1, 23.5, 24.33

[56] References Cited

U.S. PATENT DOCUMENTS 5,075,216  12/1991  Innis et al. .................. 435/6
5,281,519  1/1994   Schechter et al. ............ 435/6

FOREIGN PATENT DOCUMENTS

WO 94/08048  4/1994  WIPO.

OTHER PUBLICATIONS

Chen et al. Acta Haematologia 90:177–181 (1993).
Adams et al. American Journal of Hematology 45:279–282 (1994).
Borriello et al. Diagnostic Molecular Pathology 3(4):246–254 (Dec. 1994).
Nath et al., "Enzyme Studies for Carbohydrate Metabolism In Thalassaemia and Some Other Clinical Conditions," *Enzymologia* 31(5):296–308 (1966).
Cossu et al., "HLA and 5' HVR insulin gene polymorphisms in thalassemia major patients with diabetes mellitus," *Diabetes Nutrition & Metabolism Clinical & Experimental*, 4(2):101–6 (Jun. 1991).
Harano et al., "HB Kurosaki: a new alpha chain variant found in Japanese woman," *Hemoglobin*, 19(3 & 4):197–201 (1995).

Miyashita, et al., "HB Kanagawa: A new alpha chain variant with an increased oxygen affinity," *Hemoglobin*, 16(1 & 2):1–10 (1992).
Powars, "Sickle Cell Anemia: Beta-S-Gene-Cluster Haplotypes as Prognostic Indicators of Vital Organ Failure," *Seminars in Hematology*, 28(3):202–8 (Jul. 1991).
Witte, "Hereditary Hemochromatosis: Chemistry and Laboratory Leadership Aids Early Detection," *American Association for Clinical Chemistry Endo*, 13(1):13–22 (Jan. 1995).
Gordeuk, et al., "Iron Overload In Africa—Interaction between a Gene and Dietary Iron Content," *The New England Journal of Medicine*, 326(2):95–100 (Jan. 9, 1992).
Alberts et al., *Molecular Biology of the Cell*, Second Edition, New York: Garland Publishing, pp. 270–271, (1989).
Bauer et al., "Genital Human Papillomavirus Infection in Female University Students as Determined by a PCR–Based Method," *JAMA*, 265(4):472–477 (Jan. 23/30 1991).
Baysal and Huisman, "Detection of Common Deletional α-Thalassemia-2 Determinants by PCR," *Am. J. Hematol.*, 46:208–213 (1994).

(List continued on next page.)

*Primary Examiner*—W. Gary Jones
*Assistant Examiner*—Debra Shoemaker
*Attorney, Agent, or Firm*—Marshall, O'Toole, Gerstein, Murray & Borun

[57] ABSTRACT

The invention is based on the discovery that adults having a genotype comprising a hemoglobin α-gene deletion are significantly more likely to be hypertensive than adults having a normal (αα/αα) gentoype. The invention provides an improved method for determining a human subject's genotype at the α-gene loci; a method of screening a human subject for an increased potential of developing hypertension and other blood-related disorders; and provides an apparatus/kit for screening a human subject for a risk of developing hypertension and other blood-related disorders.

39 Claims, 4 Drawing Sheets

OTHER PUBLICATIONS

Bowden et al., "A PCR–based strategy to detect the common severe determinants of α thalassaemia," *Br. J. Haematol.*, 81:104–108 (1992).

Bowie et al., "Detection of α–Thalassemias by Multiplex Polymerase Chain Reaction," *Clin. Chem.*, 40(12):2260–2266 (1994).

Bowie et al., "Diagnosis of Alpha Thalassemia Syndromes Using Multiplex Polymerase Chain Reaction (M–PCR) Methods," *Annales de Biologie Clinque* 51:422 (1993) (ABSTRACT 152).

Crowley et al., "Whole Blood Viscosity in Beta Thalassemia Minor," *Annals. Clin. Lab. Sci.*, 22(4):229–235 (1992).

Dode et al., "Locus assignment of human α globin mutations by selective amplification and direct sequencing," *Br. J. Haematol.*, 76:275–281 (1990).

Dozy et al., "α–Globin gene organisation in blacks precludes the severe form of α–thalassaemia," *Nature*, 280:605–607 (Aug. 16, 1979).

Drmanac et al., "DNA Sequence Determination by Hybridization: A Strategy for Efficient Large–Scale Sequencing," *Science*, 260:1649–1652 (Jun. 11, 1993).

Embury et al, "Two Different Molecular Organizations Account for the Single α–Globin Gene of the α–Thalassemia–2 Genotype," *J. Clin. Invest.*, 66:1319–1325 (Dec. 1980).

Fowlow et al., "A Medical Genetic Survey of a Hutterite Population," *Can. J. Gen. Cytol.* 15(3):657 (1973).

GENBANK Report for Locus HUMHBA1, "Human Alpha Globin Gene Cluster on Chromosome 16: Zeta Gene," Accession Nos. J00182 and J00181, (Nov. 17, 1994).

GENBANK Report for Locus HUMHBB, "Human Beta Globin Region on Chromosome 11," Accession Nos. U01317, J00179, J00093, J00094, J00096, J00158, J00159, J00160, J00161, J00162, J00163, J00164, J00165, J00166, J00167, J00168, J00169, J00170, J00171, J00172, J00173, J00174, J00175, J00177, J00178, K01239, K01890, K02544, M18047, M19067, M24868, M24886, X00423, X00424, X00672 (Jan. 20, 1994).

Grim et al., "High Blood Pressure in Blacks: Salt, Slavery, Survival, Stress, and Racism," *Hypertension: Pathophysiology, Diagnosis, and Management. Second Edition*, Laragh and Brenner (Eds.), New York: Raven Press, Ltd., Chapter 12 (1995).

Higgs, "The thalassaemia syndromes," *Q.J. Med.*, 86:559–564 (1993).

Higgs et al., "A Review of the Molecular Genetics of the Human α–Globin Gene Cluster," *Blood*, 73(5):1081–1104 (Apr. 1989).

Higgs et al., "Independent recombination events between the duplicated human α globin genes; implications for their concerted evolution," *Nucl. Acids Res.*, 12(18):6965–6977 (1984).

James and Baker, "Human Population Biology and Blood Pressure: Evolutionary and Ecological Considerations and Interpretations of Population Studies," *Hypertension: Pathophysiology, Diagnosis, and Management. Second Edition*, Laragh and Brenner (Eds.), New York: Raven Press, Ltd., Chapter 8 (1995).

Kan, "Development of DNA Analysis for Human Diseases: Sickle Cell Anemia and Thalassemia as a Paradigm," *JAMA*, 267(11):1532–1536 (Mar. 18, 1992).

Kazazian, "The Thalassemia Syndromes: Molecular Basis and Prenatal Diagnosis in 1990," *Sem. Hemotol.*, 27(3):209–228 (Jul. 1990).

Lebo et al., "Prenatal diagnosis of α–thalassemia by polymerase chain reaction and dual restriction enzyme analysis," *Hum. Gen.*, 85:293–299 (1990).

Leckie, "High Blood Pressure: Hunting the Genes," *Bio–Essays*, 14(1):37–41 (Jan. 1992).

Lewin and Stewart–Haynes, "A Simple Method for DNA Extraction from Leukocytes for Use in PCR," *BioTechniques*, 13(4):522–523 (1992).

Liehaber, "α Thalassemia," *Hemoglobin*, 13(7&8):685–731 (1989).

Lubin et al., "Precise gene dosage determination by polymerase chain reaction: theory, methodology, and statistical approach," *Mol. Cell. Probes*, 5:307–317 (1991).

Lundeberg et al., "Rapid Colorimetric Quantification of PCR–Amplified DNA," *BioTechniques*, 10(1):68–75 (1991).

McCarron et al., "High Blood Pressure," *Scientific American Medicine*, New York, Scientific American, Inc., Chapter 1, Part VII, pp. 1–32 (1993).

Mirzabekov, "DNA sequencing by hybridization–a mega sequencing method and a diagnostic tool?," *TIBTECH*, 12:27–32 (Jan. 1994).

Nagabhusban et al., "Molecular Diagnosis of Alpha Thalassemia and Beta Chain Hemoglobinopathies Using Multiplex PCR (MPCR) and Automated DNA Sequencing," *Clin. Chem.* 38:1182 (1993) (ABSTRACT 0291).

Nierman, et al. (eds.), *ATCC/NIH Repository Catalogue of Human and Mouse DNA Probes and Libraries*, Seventh Edition, American Type Culture Collection, Rockville, Maryland, p. 117, (1993).

Reddy et al., "An Association Between Hypertension and the 'Silent Carrier' State for Alpha Thalassemia," The 1994 San Diego Conference: The Genetic Revolution, San Diego, CA, Nov. 18, 1994 (ABSTRACT ONLY).

Sambrook et al., *Molecular Cloning–A laboratory Manual, Second Edition*, Cold Spring Harbor: Cold Spring Harbor Press, Chapters 7, 9, 13 (1989).

Schrier and Mohandas, "Globin–Chain Specificity of Oxidation–Induced Changes in Red Blood Cell Membrane Properties," *Blood*, 79(6):1586–1592 (Mar. 15, 1992).

Schultz et al., "A role for endothelin and nitric oxide in the pressor response to diaspirin cross–linked hemoglobin," *J. Lab. Clin. Med.*, 122(3):301–308 (Sep. 1993).

Wang et al., "Myocardial Infarction and thalassemia Trait: An Example of Heterozygote Advantage," *Amer. J. Hematol.* 49:73–75 (1995).

Williamson, "The Molecular Basis of Human Genetic Disease–Deletion, Misprocessing, Termination," *J. Cell Biochem.* 0(9Part A):31 (1985) (ABSTRACT 0069).

Amplicon size (base pairs)

Amplicon size (base pairs)

5,750,345

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 12847 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: join(6703..6797, 6915..7119, 7262..7387)

( i x ) FEATURE:
        ( A ) NAME/KEY: CDS
        ( B ) LOCATION: join(10514..10608, 10726..10930, 11080..11205)

( x i ) SEQUENCE DESCRIPTION: SEQ ID NO:1:

```
GGATCCCCGG  GGCTCTGGGC  GGTGTGGGCG  TAGTGAAGCC  CCACGCAGCC  GCCCTCCTCC      60
CCGGTCACTG  ACTGGTCCTG  CAGGCTCTTC  ACGGTGTACC  CCAGCACCAA  GGTCTACTTC     120
CCGCACCTGA  GCGCCTGCCA  GGACGACGCA  GCTGCTGAGC  CACGGGAGCG  CATCTGCGGC     180
TGTGGCGCGG  CGGTGCAGCA  CGTGGACAAC  CTGCGCGCCT  GAGCCCGCTG  GCGGACCTGA     240
CGCTCGTTGC  GCGTGGACCC  AGCCAACTTT  CCGGTGAGGC  CTTTCCGGCC  GGGGCAATGG     300
TGCATCGCCT  AGCCGGGATG  GGGGGGCTCT  GGGGGTCCCT  AGCGGGGCAG  ACCCCGTCTC     360
ACCGGCCCCT  TCTCCTGCAG  CTGCTAATCC  AGTGTTTCCA  CGTCGTGCTG  GCCTCCCACC     420
TGCAGGACGA  GTTCACCGTG  CAAATGCAAG  CGGCGTGGGA  CAAGTTCCTG  ACTGGTGTGG     480
CCGTGGTGCT  GACCGAAAAA  TACGCTGAGC  CCTGTGCTGC  GAGGCCTTGG  TCTGTGCATG     540
TCAATAAACA  GAGGCCCGAA  CCATCTGCCC  CTGCCTGTGT  GGTCTTTGGG  GAGCTAGCAA     600
AGCGAGGTCA  CTATTGTTGG  CCAGTAAGCT  CAGGGACCTA  AAGGGAGCCT  CCTAGAACTC     660
TCAAATGCGC  CCCACCCCCG  GAGGTTTGTC  CTCCCATGGC  GAGGAGTGCG  ATGGGGCAGA     720
GGGAGCAGTG  TGATATGGCG  GGGGTAGAGA  GGGTGGCCTT  CGACTTCAAA  CCCTTGACTC     780
GGGCTTCGAA  CCATACTCGT  TCGCAAAGCA  GTTCCCCATT  CATGCATTTA  TTCAGTTCAT     840
TCCTTCCCTC  CATCCCCATT  TCCTGCTGGG  ACCTGTAGAT  GCTAATCCTG  GCCCTTTTTG     900
```

-continued

| | | | | | |
|---|---|---|---|---|---|
| CAGAGAGATG | CAGAAACTGA | GGTCCCAGAG | CCAAATGTGC | AACCTAATTC | GTTGGCCAGA | 960 |
| GCAGAGGGCC | GCAGACCTGT | TCCTTTCCCC | TTCCTTCCCC | CATGGACACT | TCCTCAGTGG | 1020 |
| CAAACCTGCG | CTAGCCTGGT | TAGCCCTCCC | TGTGACCCTG | CAGCCCTGGG | GATGAGGTCG | 1080 |
| GGAGGAAGAC | CTCAGTGGCC | ACAATTGGC | AGACAGAGAG | GTTTAGTCTT | CCAGCCTGCT | 1140 |
| CAATGACAAG | CTGTGCGACC | CTGGGCTGTC | CCAGAGCTCT | AGGCCTTTAC | CTATCGAATA | 1200 |
| GAAAAACAGC | GTCCAACTCA | TGAGATTTTT | GAAATAATTT | TTGAAATCAT | AACACAGGGT | 1260 |
| GGGTGCCTGC | AGGGACGTTG | CCACCCCACC | CCTCCACCCA | GCCCAGCTG | CCGTGTCTCA | 1320 |
| ATCTCTGCAG | GTGCCAGGC | CAAGGCATTC | CCTTCCCCAG | GCTCCCTCTT | CTCCCTCCCC | 1380 |
| AAGGATTGGG | AAGGGAATCT | TAGGGCTCCA | CCCCAGGCTT | TTCAGACAAA | GAATAGGGGC | 1440 |
| TCAGGAAAGA | TTGGGACCTT | GGAGTTCTCC | AATCCCTAAT | AGGGTTGGGT | GTGGGTTGGG | 1500 |
| CATCCTGGGT | GTGTGTGGGG | AGCACCTGGA | CCAGGCCTGG | CACCCAGGTC | TGACCTGGCA | 1560 |
| GTCAGCAATG | AGGTCTGAAG | AGAGCTGCTG | GAAGTGGAGC | CCTGACTGTG | AGTCGGCCAA | 1620 |
| ACTCCCCCCA | GCAGTCAGTG | CCACAGACCT | GTTGCCCTGC | ACTGCCTGGG | ACCCCAGCCC | 1680 |
| GGTAGTTTGG | AGAACTTGGC | CCCTCGTTAT | CTACATCCCC | CAAGTGTTTT | TTTGTTTTTG | 1740 |
| GGGGTTTTTT | TTTTTTTTTT | TTTGCTTTGT | TTTTGTTTTT | GAGATAGGCC | CTTGCTCTGA | 1800 |
| CACCCCGGCT | GGAGTGCAGT | GGCAAGTTTT | GGCTCACTGC | AGCCTCAACC | TCCTGGGTTC | 1860 |
| AAGCGATTCT | CCTGCCTCTG | TCTCCCGTGT | AGCTGGGATT | ACAGGCATGG | CCGCCATTC | 1920 |
| CTGGCTAATT | TATGTATTTT | TAATAGAGAC | ACAGTTCAC | CATGTTGATC | AGGCTGGTCT | 1980 |
| CAAACTCCTG | ACCTCAAGTG | ATCTGCCCTC | CTGGTCTCCC | AAAGTGCTGG | GATGACAGGC | 2040 |
| GTGAGCCACC | ACACCCAGCC | CCCGCAACTG | TTTACATGGA | TAATTAACAA | GCTTTTGTC | 2100 |
| CCAGGCAGAG | TTTGGTGTGA | AAGCAGCTTA | TGTTTCACTT | TGGAAAAACT | GTGCTCTTCT | 2160 |
| CCCCATCCAG | GAAGCTGCCT | GGGTCTGGGC | CATATGTGGA | TACCTTATGG | GTATAAGCTG | 2220 |
| CTCAGGACCC | TGTGTGGAAG | CTCAGGACAA | TGCCAGCGGG | AAGGCTACCA | TGTGGAGAGC | 2280 |
| TGTCTCTGTT | TGGGCAGGAC | TAAGAGACGC | AGGGAACCTT | GGGAACCTGT | CTACTCTCAC | 2340 |
| TCACTCCTCC | TCCCCTTTCC | TTCCAGGCAC | CTCTGCAACT | TGCCAGCCAA | TGACCCTGCA | 2400 |
| TCCCAGGCAT | AAGAGCTCCT | ACTCTCCCCC | ACCTTTCACT | TTTGAGCTTA | CACAGACTCA | 2460 |
| GAAATTAAGC | TGCCGTGGTG | CTGTCTCCTG | AGGACAAGGC | TAACACCAAG | GCGGTCTGGG | 2520 |
| AGAAAGTTGG | CGACCACACT | GCTGGCTATG | CCACGGAGGC | CCTGGAGAGG | CAAGAACCCT | 2580 |
| CCTCTCCCTG | CTCACACCTT | GGGTCCAACG | CCCACTCCAG | GGCTCCACTG | CCACCCCTA | 2640 |
| ACTATTCTTA | CCCTGGACCC | AGCCCCAGC | CCCTCACTCT | TTGCTTCCCC | CTGAAGCATG | 2700 |
| TTCCTGACCT | TCCTCTCACT | TGGCCCTGAG | TTATGGCTCA | GCCCAGATCA | AGAAACAATG | 2760 |
| CAAGTAGGTG | GCCGACACGC | TGACCAATGC | CGTGGTCCAC | TTAGATGACA | TGCCCAATGA | 2820 |
| TGTGTCTGAG | GTGAGGAAGC | TGCATGTCCA | CGAGCTGTGG | GTGGACCCAG | GCAACATCAG | 2880 |
| GGAGAGCTTT | GGGCTGGGAG | GAATCTAGGG | TGTGGGGGCA | GCTGGCCTTC | CTCATAGGAC | 2940 |
| AGACCCTCCC | ACGCGTTCAG | GGAGGTGGAG | CACAGGTGGC | AGTAGTATCT | GCATCCCCTG | 3000 |
| ACTCTCTCTC | CACAGTTCCT | GGGTAAATGC | CTGCTGGTGA | CCTAGGCCTG | CCACACCCTT | 3060 |
| CCCGGTTTAC | CCATGTGGTG | CCTCCATGGA | CAAATTATTT | GCTTTGTGA | GTGCTGTGTT | 3120 |
| GACCTAAAAA | CACCATTAAG | CTAGAGCATT | GGTGGTCATG | CCCCTGCCT | GCTGGGCCTC | 3180 |
| CCACCAGGCC | CGCCTCCCCT | CCCTGCCCCA | GCACTTCCTG | ATCTTTGAAT | GAAGTCCGAG | 3240 |
| TAGGCAGCAG | CCTGTGTGTG | CCTGGGTTCT | CTCTGTCCCG | GAATGTGCCA | ACAGTGGAGG | 3300 |

```
TGTTTACCTG TCTCAGACCA AGGACCTCTC TGCAGCTGCA TGGGGCTGGG GAGGGAGAAC    3360
TGCAGGGAGT ATGGGAGGGG AAGCTGAGGT GGGCCTGCTC AAGAGAAGGT GCTGAACCAT    3420
CCCCTGTCCT GAGAGGTGCC AGGCCTGCAG GCAGTGGCTC AGAAGCTGGG GAGGAGAGAG    3480
GCATCCAGGG TTCTACTCAG GGAGTCCCAG CATCGCCACC CTCCTTTGAA ATCTCCCTGG    3540
TTGAACCCAG TTAACATACG CTCTCCATCA AAACAAAACG AAACAAAACA AACTAGCAAA    3600
ATAGGCTGTC CCCAGTGCAA GTGCAGGTGC CAGAACATTT CTCTCATTCC CACCCCTTCC    3660
TGCCAGAGGG TAGGTGGCTG GAGTGAGGGT GCTGGCCCTA CTCACACTTC CTGTGTCATG    3720
GTGACCCTCT GAGAGCAGCC CAGTCAGTGG GGAAGGAGGA AGGGGCTGGG ATGCTCACAG    3780
CCGGCAGCCC ACACCTAGGG AGACTCTTCA GCAGAGCACC TTGCGGCCTT ACTCCTGCAC    3840
GTCTCCTGCA GTTTGTAAGG TGCATTCAGA ACTCACTGTG TGCCCAGCCC TGAGCTCCCA    3900
GCTAATTGCC CCACCCAGGG CCTCTGGGAC CTCCTGGTGC TTCTGCTTCC TGTGCTGCCA    3960
GCAACTTCTG GAAACGTCCC TGTCCCCGGT GCTGAAGTCC TGGAATCCAT GCTGGGAAGT    4020
TGCACAGCCC ATCTGGCTCT CAGCCAGCCT AGGAACACGA GCAGCACTTC CAGCCCAGCC    4080
CCTGCCCCAC AGCAAGCCTC CCCCTCCACA CTCACAGTAC TGAATTGAGC TTTGGGTAGG    4140
GTGGAGAGGA CCCTGTCACC GCTTTTCTTC TGGACATGGA CCTCTCTGAA TTGTTGGGGA    4200
GTTCCCTCCC CCTCTCCACC ACCCACTCTT CCTGTGCCTC ACAGCCCAGA GCATTGTTAT    4260
TTCAACAGAA ACACTTTAAA AATAAACTA  AAATCCGACA GGCACGGTGG CTCACACCTG    4320
TAATCCCAGT ACTTTGGGAG GCTGAGGCGA GAGGATCACC TGAGGTCGGG AGTTTGAGAC    4380
CAGCCTGACC AATATGGAGA AACCCCAGTT ATACTAAAAA TACAAAATTA GCTGGGTGTG    4440
GTGGCGCATG CCTGTAATCC TAGCTACTAG GAAGGCTGAG GCAGGAGAAT CGCTTGAACC    4500
CGGGAGGTGG AGGTTGAGGT GAGCCGAGAT CACGCCATTG CACTCCAGCC TGGGCAACAA    4560
GAGCAAAACT CCGTCTCAAA AATAAATAA  ATAAATAAAT AAATAAACTA AAATCTATCC    4620
ATGCTTTCAC ACACACACAC ACACACACAC ACACACACCT TTTTGTGTT  ACTAAAGTAG    4680
GAGAGTGTCT CTCTTTCCTG TCTCCTCACA CCCACCCCCA GAAGAGACCA AAATGAAGGG    4740
TTTGGAACTC ACGCCATGGG CCCCATCCCA TGCTGAGGGA ACACAGCTAC ATCTACAACT    4800
ACTGCCACAG CGTCTCTTTT TGGACACCCC TACCATCATA CTGTAGATAC CCGTGTACAA    4860
CCTTCCTATT CTCAGTGAAG TGTCTCCCCT GCATCCCTTT CAGCCAGTTC ATTCAGCTCT    4920
GCTCGCCCAT TCCACAGTCT CACTGATTAT TACTATGTTT CCATCATGAT CCCCCCAAAA    4980
AATCATGACT TTATTTTTTT ATTTTTATTA TTATTATTAT TTTTTTTTT  TTTTTGAGA    5040
CGGAGTCTCG CTCTGTGACC CAGGCTGGAG TGCAGTGGCA AATCTCGGCT CACTGCAAGC    5100
TCCACCTCGC AGGTTCACGC CATTCTCCTC CCTCAGCCTC CCGAGTCGCT GAGTAGCTGG    5160
GCTACAGCGC CCCCACTAG  TCGTGGCTAA TTTTTTCTTT TTTAATAGA  GACAGAGTTT    5220
CACTGCATTA GCGAGGATGG TCTCGATCTC CTGACCTCGC ATCTGCCAGC CTCAGCCTTC    5280
CAATGTGCTG GGATTACAGC GTGAGCCAAC GCGCCCGGCC TTATATATTT ATTTTTTGA    5340
GACAGAGTCT CGCTGTGTCG TCAGGCTAGA GTGCTGTGGC ACGATCTCGG CTCACTGCAA    5400
CCTCCAACTC CCTGGTTCAA AGGATTCTCC AGCCTCACC  TCCCGAGTAG CTGGGATTAC    5460
AGGCGTGCAC CACCACACCA GCTAATTTTT GTATTTTTAG TAGAGACGGG GTTTCTCCAT    5520
GTTGGTCAGC CTGGTCTCGA ACTCCCGACC ACAGCTGATC CCACCCACCT CGGCCTCCCA    5580
AAGTGCTGGG ATTCCAGGCG TGCGCCGAGC CTGGCCAAAC CATCACTTTT CATGAGCAGG    5640
GATGCACCCA CTGGACTCCT GGACCTCCCA CCCTCCCCCT CGCCAAGTCC ACCCCTTCCT    5700
```

```
TCCTCACCCC ACATCCCCTC ACCTACATTC TGCAACACAG GGGCCTTCTC TCCCCTGTCC         5760

TTTCCCTACC CAGAGCCAGG TTTGTTTATC TGTTTACAAC CAGTATTTAC CTAGCAAGTC         5820

TTCCATCAGA TAGCATTTGG AGAGCTGGGG GTGTCACAGT GAACCACGAC CTCTAGGCCA         5880

GTGGGAGAGT CAGTCACACA AACTGTGAGT CCATGACTTG GGGCTTAGCC AGTACCCACC         5940

ACCCCACGCG CCACCCCACA ACCCCGGGTA GAGGAGTCTG AATCTGGAGC CGCCCCCAGC         6000

CCAGCCCCGT GCTTTTTGCG TCCTGGTGTT TGTTCCTTCC CGGTGCCTGT CACTCAAGCA         6060

CACTAGTGAC TATCGCCAGA GGGAAAGGGA GCTGCAGGAA GCGAGGCTGG AGAGCAGGAG         6120

GGGCTCTGCG CAGAAATTCT TTTGAGTTCC TATGGGCCAG GGCGTCCGGG TGCGCGCATT         6180

CCTCTCCGCC CCAGGATTGG GCGAAGCCCT CCGGCTCGCA CTCGCTCGCC CGTGTGTTCC         6240

CCGATCCCGC TGGAGTCGAT GCGCGTCCAG CGCGTGCCAG GCCGGGGCGG GGGTGCGGGC         6300

TGACTTTCTC CCTCGCTAGG GACGCTCCGG CGCCCGAAAG GAAAGGGTGG CGCTGCGCTC         6360

CGGGGTGCAC GAGCCGACAG CGCCCGACCC CAACGGGCCG GCCCCGCCAG CGCCGCTACC         6420

GCCCTGCCCG GGCGAGCGGG ATGGGCGGGA GTGGAGTGGC GGGTGGAGGG TGGAGACGTC         6480

CTGGCCCCCG CCCCGCGTGC ACCCCAGGG GAGGCCGAGC CCGCCGCCCG GCCCCGCGCA         6540

GGCCCCGCCC GGGACTCCCC TGCGGTCCAG GCCGCGCCCC GGGCTCCGCG CCAGCCAATG         6600

AGCGCCGCCC GGCCGGGCGT GCCCCGCGC CCCAAGCATA AACCCTGGCG CGCTCGCGGC         6660

CCGGCACTCT TCTGGTCCCC ACAGACTCAG AGAGAACCCA CC ATG GTG CTG TCT         6714
                                                  Met Val Leu Ser
                                                   1

CCT GCC GAC AAG ACC AAC GTC AAG GCC GCC TGG GGT AAG GTC GGC GCG         6762
Pro Ala Asp Lys Thr Asn Val Lys Ala Ala Trp Gly Lys Val Gly Ala
 5               10                  15                  20

CAC GCT GGC GAG TAT GGT GCG GAG GCC CTG GAG AG  GTGAGGCTCC              6807
His Ala Gly Glu Tyr Gly Ala Glu Ala Leu Glu Arg
             25                  30

CTCCCCTGCT CCGACCCGGG CTCCTCGCCC GCCCGGACCC ACAGGCCACC CTCAACCGTC         6867

CTGGCCCCGG ACCCAAACCC CACCCCTCAC TCTGCTTCTC CCCGCAG G ATG TTC           6921
                                                     Met Phe

CTG TCC TTC CCC ACC ACC AAG ACC TAC TTC CCG CAC TTC GAC CTG AGC         6969
Leu Ser Phe Pro Thr Thr Lys Thr Tyr Phe Pro His Phe Asp Leu Ser
 35                  40                  45                  50

CAC GGC TCT GCC CAG GTT AAG GGC CAC GGC AAG AAG GTG GCC GAC GCC         7017
His Gly Ser Ala Gln Val Lys Gly His Gly Lys Lys Val Ala Asp Ala
             55                  60                  65

CTG ACC AAC GCC GTG GCG CAC GTG GAC GAC ATG CCC AAC GCG CTG TCC         7065
Leu Thr Asn Ala Val Ala His Val Asp Asp Met Pro Asn Ala Leu Ser
         70                  75                  80

GCC CTG AGC GAC CTG CAC GCG CAC AAG CTT CGG GTG GAC CCG GTC AAC         7113
Ala Leu Ser Asp Leu His Ala His Lys Leu Arg Val Asp Pro Val Asn
     85                  90                  95

TTC AAG GTGAGCGGCG GGCCGGGAGC GATCTGGGTC GAGGGGCGAG ATGGCGCCTT         7169
Phe Lys
100

CCTCTCAGGG CAGAGGATCA CGCGGGTTGC GGGAGGTGTA GCGCAGGCGG CGGCTGCGGG         7229

CCTGGGCCGC ACTGACCCTC TTCTCTGCAC AG CTC CTA AGC CAC TGC CTG CTG         7282
                                   Leu Leu Ser His Cys Leu Leu
                                                 105

GTG ACC CTG GCC GCC CAC CTC CCC GCC GAG TTC ACC CCT GCG GTG CAC         7330
Val Thr Leu Ala Ala His Leu Pro Ala Glu Phe Thr Pro Ala Val His
         110                 115                 120

GCC TCC CTG GAC AAG TTC CTG GCT TCT GTG AGC ACC GTG CTG ACC TCC         7378
```

```
Ala Ser Leu Asp Lys Phe Leu Ala Ser Val Ser Thr Val Leu Thr Ser
    125                 130                 135

AAA TAC CGT TAAGCTGGAG CCTCGGTAGC CGTTCCTCCT GCCCGATGGG                7427
Lys Tyr Arg
140

CCTCCCAACG GGCCCTCCTC CCCTCCTTGC ACCGGCCCTT CCTGGTCTTT GAATAAAGTC      7487

TGAGTGGGCG GCAGCCTGTG TGTGCCTGGG TTCTCTCTGT CCCGGAATGT GCCAACAATG      7547

GAGGTGTTTA CCTGTCTCAG ACCAAGGACC TCTCTGCAGC TGCATGGGGC TGGGGAGGGA      7607

GAACTGCAGG GAGTATGGGA GGGGAAGCTG AGGTGGGCCT GCTCAAGAGA AGGTGCTGAA      7667

CCATCCCCTG TCCTGAGAGG TGCCAGGCCT GCAGGCAGTG GCTCAGAAGC TGGGGAGGAG      7727

AGAGGCATCC AGGGTTCTAC TCAGGGAGTC CCAGCATCGC CACCCTCCTT TGAAATCTCC      7787

CTGGTTGAAC CCAGTTAACA TACGCTCTCC ATCAAAACAA AACGAAACAA AACAAACTAG      7847

CAAAATAGGC TGTCCCCAGT GCAAGTGCAG GTGCCAGAAC ATTTCTCTCA TTCCCACCCC      7907

TTCCTGCCAG AGGGTAGGTG GCTGGAGTGA GGGTGCTGGC CCTACTCACA CTTCCTGTGT      7967

CACGGTGACC CTCTGAGAGC AGCCCAGTCA GTGGGGAAGG AGGAAGGGGC TGGGATGCTC      8027

ACAGCCGGCA GCCCACACCT AGGGAGACTC TTCAGCAGAG CACCTTGCGG CCTTACTCCT      8087

GCACGTCTCC TGCAGTTTGT AAGGTGCATT CAGAACTCAC TGTGTGCCCA GCCCTGAGCT      8147

CCCAGCTAAT TGCCCCACCC AGGGCCTCTG GGACCTCCTG GTGCTTCTGC TTCCTGTGCT      8207

GCCAGCAACT TCTGGAAACG TCCCTGTCCC CGGTGCTGAA GTCCTGGAAT CCATGCTGGG      8267

AAGTTGCACA GCCCATCTGG CTCTCAGCCA GCCTAGGAAC ATGAGCAGCA CTTCCAACCC      8327

AGTCCCTGCC CCACAGCAAG CCTCCCCTC CACACTCACA GTACTGGATT GAGCTTTGGG       8387

GAGGGTGGAG AGGACCCTGT CACCGCTTTC CTTCTGGACA TGGACCTCTC TGAATTGTTG     8447

GGGAGTTCCC TCCCCCTCTC CACCACCCGC TCTTCCTGCG CCTCACAGCC CAGAGCATTG      8507

TTATTTCAGC AGAAACACTT TAAAAAATAA ACTAAAATCC GACAGGCACG GTGGCTCACG      8567

CCTGTAATCC CAGCACTTTG GGAGGCCGAG GTGGGAGGAT CACCTGAGGT CGGGAGTTTG      8627

AGACCACCCT GATCAACATG TAGAAACCCC ATCTATACTA AAAATACAAA ATCAGCCGGG      8687

CATGGTGGCC CATGCCTGTA AACCCACCTA CTCCGGAGGC TGAGGCAGGA GAATCATTTT      8747

AACCAAGGAG GCAGAGGTTG CAGTGAGCTA AGATCACACC ATTGCACTCC AGCCTGGAAA     8807

ACAACAGCGA AACTCCGCCT CAAAAAAAA AAAGCCCCCA CATCTTATCT TTTTTTTTC       8867

CTTCAGGCTG TGGGCAGAGT CAGAAAGTCA GAAGAGGGTG GCAGACAGGG AGGGGAAATG     8927

AGAAGATCCA ACGGGGGAAG CATTGCTAAG CTGGTCGGAG CTACTTCCTT CTCTGCCCAA     8987

GGCAGCTTAC CCTGGCTTGC TCCTGGACAC CCAGGGCAGG GCCTGAGTAA GGGCCTGGGG    9047

AGACAGGGCA GGGAGCAGGC TGAAGGGTGC TGACCTGATG CACTCCTCAA AGCAGATCTT    9107

CTGCCAGACC CCAGGAAAT GACTTATCAG TGATTTCTCA GGCTGTTTTC TCCTCAGTAC      9167

CATCCCCCA AAAACATCA CTTTTCATGC ACAGGGATGC ACCCACTGGC ACTCCTGCAC       9227

CTCCCACCCT TCCCCAGAAG TCCACCCCTT CCTTCCTCAC CCTGCAGGAG CTGGCCAGCC    9287

TCATCACCCC AACATCTCCC CACCTCCATT CTCCAACCAC AGGGCCCTTG TCTCCTCTGT    9347

CCTTTCCCCT CCCCGAGCCA AGCCTCCTCC CTCCTCCACC TCCTCCACCT AATACATATC    9407

CTTAAGTCTC ACCTCCTCCA GGAAGCCCTC AGACTAACCC TGGTCCCCTT GAATGCCTCG    9467

TCCACACCTC CAGACTTCCT CAGGGCCTGT GATGAGGTCT GCACCTCTGT GTGTACTTGT    9527

GTGATGGTTA GAGGACTGCC TACCTCCCAG AGGAGGTTGA ATGCTCCAGC CGGTTCCAGC    9587

TATTGCTTTG TTTACCTGTT TAACCAGTAT TTACCTAGCA AGTCTTCCAT CAGATAGCAT    9647
```

```
TTGGAGAGCT GGGGGTGTCA CAGTGAACCA CGACCTCTAG GCCAGTGGGA GAGTCAGTCA     9707

CACAAACTGT GAGTCCATGA CTTGGGGCTT AGCCAGCACC CACCACCCCA CGCGCCACCC     9767

CACAACCCCG GGTAGAGGAG TCTGAATCTG GAGCCGCCCC CAGCCCAGCC CCGTGCTTTT     9827

TGCGTCCTGG TGTTTATTCC TTCCCGGTGC CTGTCACTCA AGCACACTAG TGACTATCGC     9887

CAGAGGGAAA GGGAGCTGCA GGAAGCGAGG CTGGAGAGCA GGAGGGGCTC TGCGCAGAAA     9947

TTCTTTTGAG TTCCTATGGG CCAGGGCGTC CGGGTGCGCG CATTCCTCTC CGCCCCAGGA    10007

TTGGGCGAAG CCCTCCGGCT CGCACTCGCT CGCCCGTGTG TTCCCCGATC CCGCTGGAGT    10067

CGATGCGCGT CCAGCGCGTG CCAGGCCGGG GCGGGGGTGC GGGCTGACTT TCTCCCTCGC    10127

TAGGGACGCT CCGGCGCCCG AAAGGAAAGG GTGGCGCTGC GCTCCGGGGT GCACGAGCCG    10187

ACAGCGCCCG ACCCCAACGG GCCGGCCCCG CCAGCGCCGC TACCGCCCTG CCCGGGCGAG    10247

CGGGATGGGC GGGAGTGGAG TGGCGGGTGG AGGGTGGAGA CGTCCTGGCC CCGCCCCGC    10307

GTGCACCCCC AGGGGAGGCC GAGCCCGCCG CCCGGCCCCG CGCAGGCCCC GCCCGGGACT    10367

CCCCTGCGGT CCAGGCCGCG CCCCGGGCTC CGCGCCAGCC AATGAGCGCC GCCCGGCCGG    10427

GCGTGCCCCC GCGCCCCAAG CATAAACCCT GGCGCGCTCG CGGCCCGGCA CTCTTCTGGT    10487

CCCCACAGAC TCAGAGAGAA CCCACC ATG GTG CTG TCT CCT GCC GAC AAG ACC     10540
                             Met Val Leu Ser Pro Ala Asp Lys Thr
                              1                   5

AAC GTC AAG GCC GCC TGG GGT AAG GTC GGC GCG CAC GCT GGC GAG TAT     10588
Asn Val Lys Ala Ala Trp Gly Lys Val Gly Ala His Ala Gly Glu Tyr
 10              15                  20                  25

GGT GCG GAG GCC CTG GAG AG  GTGAGGCTCC CTCCCCTGCT CCGACCCGGG        10638
Gly Ala Glu Ala Leu Glu Arg
                30

CTCCTCGCCC GCCCGGACCC ACAGGCCACC CTCAACCGTC CTGGCCCCGG ACCCAAACCC    10698

CACCCCTCAC TCTGCTTCTC CCCGCAG G ATG TTC CTG TCC TTC CCC ACC ACC     10750
                              Met Phe Leu Ser Phe Pro Thr Thr
                               35                      40

AAG ACC TAC TTC CCG CAC TTC GAC CTG AGC CAC GGC TCT GCC CAG GTT     10798
Lys Thr Tyr Phe Pro His Phe Asp Leu Ser His Gly Ser Ala Gln Val
            45                  50                  55

AAG GGC CAC GGC AAG AAG GTG GCC GAC GCC CTG ACC AAC GCC GTG GCG     10846
Lys Gly His Gly Lys Lys Val Ala Asp Ala Leu Thr Asn Ala Val Ala
        60                  65                      70

CAC GTG GAC GAC ATG CCC AAC GCG CTG TCC GCC CTG AGC GAC CTG CAC     10894
His Val Asp Asp Met Pro Asn Ala Leu Ser Ala Leu Ser Asp Leu His
    75                  80                      85

GCG CAC AAG CTT CGG GTG GAC CCG GTC AAC TTC AAG GTGAGCGGCG         10940
Ala His Lys Leu Arg Val Asp Pro Val Asn Phe Lys
 90                  95                  100

GGCCGGGAGC GATCTGGGTC GAGGGGCGAG ATGGCGCCTT CCTCGCAGGG CAGAGGATCA    11000

CGCGGGTTGC GGGAGGTGTA GCGCAGGCGG CGGCTGCGGG CCTGGGCCCT CGGCCCCACT    11060

GACCCTCTTC TCTGCACAG CTC CTA AGC CAC TGC CTG CTG GTG ACC CTG GCC    11112
                      Leu Leu Ser His Cys Leu Leu Val Thr Leu Ala
                                      105                 110

GCC CAC CTC CCC GCC GAG TTC ACC CCT GCG GTG CAC GCC TCC CTG GAC     11160
Ala His Leu Pro Ala Glu Phe Thr Pro Ala Val His Ala Ser Leu Asp
        115                 120                 125

AAG TTC CTG GCT TCT GTG AGC ACC GTG CTG ACC TCC AAA TAC CGT         11205
Lys Phe Leu Ala Ser Val Ser Thr Val Leu Thr Ser Lys Tyr Arg
            130                 135                 140

TAAGCTGGAG CCTCGGTGGC CATGCTTCTT GCCCCTTGGG CCTCCCCCCA GCCCCTCCTC    11265
```

-continued

```
CCCTTCCTGC ACCCGTACCC CCGTGGTCTT TGAATAAAGT CTGAGTGGGC GGCAGCCTGT      11325
GTGTGCCTGA GTTTTTTCCC TCAGAAACGT GCCAGCATGG GCGTGGACAG CAGCTGGGAC      11385
ACACATGGCT AGAACCTCTC TGCAGCTGGA TAGGGTAGGA AAAGGCAGGG GCGGGAGGAG      11445
GGGATGGAGG AGGGAAAGTG GAGCCACCGC GAAGTCCAGC TGGAAAAACG CTGGACCCTA      11505
GAGTGCTTTG AGGATGCATT TGCTCTTTCC CGAGTTTTAT TCCCAGACTT TTCAGATTCA      11565
ATGCAGGTTT GCTGAAATAA TGAATTTATC CATCTTTACG TTTCTGGGCA CTCTTGTGCC      11625
AAGAACTGGC TGGCTTTCTG CCTGGGACGT CACTGGTTTC CAGAGGTCC TCCCACATAT       11685
GGGTGGTGGG TAGGTCAGAG AAGTCCCACT CCAGCATGGC TGCATTGATC CCCCATCGTT      11745
CCCACTAGTC TCCGTAAAAC CTCCCAGATA CAGGCACAGT CTAGATGAAA TCAGGGGTGC      11805
GGGGTGCAAC TGCAGGCCCC AGGCAATTCA ATAGGGGCTC TACTTTCACC CCCAGGTCAC      11865
CCCAGAATGC TCACACACCA GACACTGACG CCCTGGGGCT GTCAAGATCA GGCGTTTGTC      11925
TCTGGGCCCA GCTCAGGGCC CAGCTCAGCA CCCACTCAGC TCCCCTGAGG CTGGGGAGCC      11985
TGTCCCATTG CGACTGGAGA GGAGAGCGGG GCCACAGAGG CCTGGCTAGA AGGTCCCTTC      12045
TCCCTGGTGT GTGTTTTCTC TCTGCTGAGC AGGCTTGCAG TGCCTGGGGT ATCAGAGGGA      12105
GGGTTCCCGG AGCTGGTAGC CATAAAGCCC TGGCCCTCAA CTGATAGGAA TATCTTTTAT      12165
TCCCTGAGCC CATGAATCAC CCTTGGTAAA CACCTATGGC AGGCCCTCTG CCTGCGTTTG      12225
TGATGTCCTT CCCGCAGCCT GTGGGTACAG TATCAACTGT CAGGAAGACG GTGTCTTCGT      12285
TATTTCATCA GGAAGAATGG AGGTCTGACC TAAAGGTAGA AATATGTCAA ATGTACAGCA      12345
GAGGGCTGGT TGGAGTGCAG CGCTTTTTAC AATTAATTGA TCAGAACCAG TTATAAATTT      12405
ATCATTTCCT TCTCCACTCC TGCTGCTTCA GTTGACTAAG CCTAAGAAAA AATTATAAAA      12465
ATTGGCCGGG CGCGGTGGCT CACACCTGTA ATTGCAGCAC TTTGCCAGGC TTAGGCAGGT      12525
GGATCACCTG AAGTCAGGGG TTCGAGACCA GCCTAGCCAA CATAGTGAAA CCCTGTCTCT      12585
ACTAAAAAGA CAAAAATTGT CCAGGTGTGA TGACTCATGC CTGTAAACCT GGCACTTTGG      12645
GAGGCGGAGG TTGTAGTGAG TCAAGATCGC GCCATCGCAC TCCAGCTTGG GCAACAAGAG      12705
CGAAACTCTG TCTCAAAAAA AAATTTAATC TAATTTAATT TAATTTAAAA ATTAGCACGG      12765
TGGTTGGGCA CAGTGGCCTC ACGCCTGTAA TCCCAGCACT TTGGGAAGCC AAGGTGGGCA      12825
GATCACAAGG TCAGGGGAAT TC                                               12847
```

( 2 ) INFORMATION FOR SEQ ID NO:2:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Val Leu Ser Pro Ala Asp Lys Thr Asn Val Lys Ala Ala Trp Gly
 1               5                  10                  15

Lys Val Gly Ala His Ala Gly Glu Tyr Gly Ala Glu Ala Leu Glu Arg
                20                  25                  30

Met Phe Leu Ser Phe Pro Thr Thr Lys Thr Tyr Phe Pro His Phe Asp
            35                  40                  45

Leu Ser His Gly Ser Ala Gln Val Lys Gly His Gly Lys Lys Val Ala
        50                  55                  60

Asp Ala Leu Thr Asn Ala Val Ala His Val Asp Asp Met Pro Asn Ala
```

|  |  |  |  | 65 |  |  |  | 70 |  |  |  | 75 |  |  |  | 80 |
| Leu | Ser | Ala | Leu | Ser | Asp | Leu | His | Ala | His | Lys | Leu | Arg | Val | Asp | Pro |
|  |  |  |  | 85 |  |  |  |  |  | 90 |  |  |  | 95 |  |
| Val | Asn | Phe | Lys | Leu | Leu | Ser | His | Cys | Leu | Leu | Val | Thr | Leu | Ala | Ala |
|  |  |  | 100 |  |  |  |  | 105 |  |  |  |  | 110 |  |  |
| His | Leu | Pro | Ala | Glu | Phe | Thr | Pro | Ala | Val | His | Ala | Ser | Leu | Asp | Lys |
|  |  | 115 |  |  |  |  | 120 |  |  |  |  | 125 |  |  |  |
| Phe | Leu | Ala | Ser | Val | Ser | Thr | Val | Leu | Thr | Ser | Lys | Tyr | Arg |  |  |
|  |  | 130 |  |  |  |  | 135 |  |  |  |  | 140 |  |  |  |

( 2 ) INFORMATION FOR SEQ ID NO:3:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Val | Leu | Ser | Pro | Ala | Asp | Lys | Thr | Asn | Val | Lys | Ala | Ala | Trp | Gly |
| 1 |  |  |  | 5 |  |  |  |  | 10 |  |  |  |  | 15 |  |
| Lys | Val | Gly | Ala | His | Ala | Gly | Glu | Tyr | Gly | Ala | Glu | Ala | Leu | Glu | Arg |
|  |  |  | 20 |  |  |  |  | 25 |  |  |  |  | 30 |  |  |
| Met | Phe | Leu | Ser | Phe | Pro | Thr | Thr | Lys | Thr | Tyr | Phe | Pro | His | Phe | Asp |
|  |  | 35 |  |  |  |  | 40 |  |  |  |  | 45 |  |  |  |
| Leu | Ser | His | Gly | Ser | Ala | Gln | Val | Lys | Gly | His | Gly | Lys | Lys | Val | Ala |
|  | 50 |  |  |  |  | 55 |  |  |  |  | 60 |  |  |  |  |
| Asp | Ala | Leu | Thr | Asn | Ala | Val | Ala | His | Val | Asp | Asp | Met | Pro | Asn | Ala |
| 65 |  |  |  | 70 |  |  |  | 75 |  |  |  |  |  |  | 80 |
| Leu | Ser | Ala | Leu | Ser | Asp | Leu | His | Ala | His | Lys | Leu | Arg | Val | Asp | Pro |
|  |  |  |  | 85 |  |  |  |  |  | 90 |  |  |  | 95 |  |
| Val | Asn | Phe | Lys | Leu | Leu | Ser | His | Cys | Leu | Leu | Val | Thr | Leu | Ala | Ala |
|  |  |  | 100 |  |  |  |  | 105 |  |  |  |  | 110 |  |  |
| His | Leu | Pro | Ala | Glu | Phe | Thr | Pro | Ala | Val | His | Ala | Ser | Leu | Asp | Lys |
|  |  | 115 |  |  |  |  | 120 |  |  |  |  | 125 |  |  |  |
| Phe | Leu | Ala | Ser | Val | Ser | Thr | Val | Leu | Thr | Ser | Lys | Tyr | Arg |  |  |
|  |  | 130 |  |  |  |  | 135 |  |  |  |  | 140 |  |  |  |

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

ACCATCCCCC CAAAAAACAT                                                        20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CTCTAACCAT CACACAAGTA                                                                      20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

ACTGGAGAGG AGAGCGGGGC                                                                      20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

AGGCTGCGGG AAGGACATCA                                                                      20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GAAGAGCCAA GGACAGGTAC                                                                      20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CAACTTCATC CACGTTCACC                                                                      20

( 2 ) INFORMATION FOR SEQ ID NO:10:

( i ) SEQUENCE CHARACTERISTICS:
        ( A ) LENGTH: 2500 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: join(687..778, 909..1131, 1982..2107)

( x i ) SEQUENCE DESCRIPTION: SEQ ID NO:10:

| | |
|---|---|
| TTTAGACATA ATTTATTAGC ATGCATGAGC AAATTAAGAA AAACAACAAC AAATGAATGC | 60 |
| ATATATATGT ATATGTATGT GTGTATATAT ACACATATAT ATATATATTT TTTTTCTTTT | 120 |
| CTTACCAGAA GGTTTTAATC CAAATAAGGA GAAGATATGC TTAGAACTGA GGTAGAGTTT | 180 |
| TCATCCATTC TGTCCTGTAA GTATTTGCA TATTCTGGAG ACGCAGGAAG AGATCCATCT | 240 |
| ACATATCCCA AAGCTGAATT ATGGTAGACA AAGCTCTTCC ACTTTTAGTG CATCAATTTC | 300 |
| TTATTTGTGT AATAAGAAAA TTGGGAAAAC GATCTTCAAT ATGCTTACCA AGCTGTGATT | 360 |
| CCAAATATTA CGTAAATACA CTTGCAAAGG AGGATGTTTT TAGTAGCAAT TTGTACTGAT | 420 |
| GGTATGGGGC CAAGAGATAT ATCTTAGAGG GAGGGCTGAG GGTTTGAAGT CCAACTCCTA | 480 |
| AGCCAGTGCC AGAAGAGCCA AGGACAGGTA CGGCTGTCAT CACTTAGACC TCACCCTGTG | 540 |
| GAGCCACACC CTAGGGTTGG CCAATCTACT CCCAGGAGCA GGGAGGGCAG GAGCCAGGGC | 600 |
| TGGGCATAAA AGTCAGGGCA GAGCCATCTA TTGCTTACAT TTGCTTCTGA CACAACTGTG | 660 |
| TTCACTAGCA ACCTCAAACA GACACC ATG GTG CAC CTG ACT CCT GAG GAG AAG | 713 |
|                                               Met Val His Leu Thr Pro Glu Glu Lys<br>                                                 1                 5 | |
| TCT GCC GTT ACT GCC CTG TGG GGC AAG GTG AAC GTG GAT GAA GTT GGT<br>Ser Ala Val Thr Ala Leu Trp Gly Lys Val Asn Val Asp Glu Val Gly<br> 10                     15                    20                    25 | 761 |
| GGT GAG GCC CTG GGC AG   GTTGGTATCA AGGTTACAAG ACAGGTTTAA<br>Gly Glu Ala Leu Gly Arg<br>               30 | 808 |
| GGAGACCAAT AGAAACTGGG CATGTGGAGA CAGAGAAGAC TCTTGGGTTT CTGATAGGCA | 868 |
| CTGACTCTCT CTGCCTATTG GTCTATTTTC CCACCCTTAG G CTG CTG GTG GTC<br>                                                                   Leu Leu Val Val<br>                                                                              35 | 921 |
| TAC CCT TGG ACC CAG AGG TTC TTT GAG TCC TTT GGG GAT CTG TCC ACT<br>Tyr Pro Trp Thr Gln Arg Phe Phe Glu Ser Phe Gly Asp Leu Ser Thr<br>                     40                            45                           50 | 969 |
| CCT GAT GCT GTT ATG GGC AAC CCT AAG GTG AAG GCT CAT GGC AAG AAA<br>Pro Asp Ala Val Met Gly Asn Pro Lys Val Lys Ala His Gly Lys Lys<br>                 55                            60                           65 | 1017 |
| GTG CTC GGT GCC TTT AGT GAT GGC CTG GCT CAC CTG GAC AAC CTC AAG<br>Val Leu Gly Ala Phe Ser Asp Gly Leu Ala His Leu Asp Asn Leu Lys<br>       70                    75                           80 | 1065 |
| GGC ACC TTT GCC ACA CTG AGT GAG CTG CAC TGT GAC AAG CTG CAC GTG<br>Gly Thr Phe Ala Thr Leu Ser Glu Leu His Cys Asp Lys Leu His Val<br>     85                       90                          95 | 1113 |
| GAT CCT GAG AAC TTC AGG GTGAGTCTAT GGGACCCTTG ATGTTTTCTT<br>Asp Pro Glu Asn Phe Arg<br>100                   105 | 1161 |
| TCCCCTTCTT TTCTATGGTT AAGTTCATGT CATAGGAAGG GGAGAAGTAA CAGGGTACAG | 1221 |
| TTAGAATGG GAAACAGACG AATGATTGCA TCAGTGTGGA AGTCTCAGGA TCGTTTAGT | 1281 |
| TTCTTTTATT TGCTGTTCAT AACAATTGTT TCTTTTGTT TAATTCTTGC TTTCTTTTTT | 1341 |
| TTCTTCTCC GCAATTTTTA CTATTATACT TAATGCCTTA ACATTGTGTA TAACAAAAGG | 1401 |
| AAATATCTCT GAGATACATT AAGTAACTTA AAAAAAAACT TTACACAGTC TGCCTAGTAC | 1461 |
| ATTACTATTT GGAATATATG TGTGCTTATT TGCATATTCA TAATCTCCCT ACTTTATTTT | 1521 |
| CTTTTATTTT TAATTGATAC ATAATCATTA TACATATTTA TGGGTTAAAG TGTAATGTTT | 1581 |
| TAATATGTGT ACACATATTG ACCAAATCAG GGTAATTTTG CATTTGTAAT TTTAAAAAAT | 1641 |
| GCTTTCTTCT TTTAATATAC TTTTTTGTTT ATCTTATTTC TAATACTTTC CCTAATCTCT | 1701 |
| TTCTTTCAGG GCAATAATGA TACAATGTAT CATGCCTCTT TGCACCATTC TAAAGAATAA | 1761 |

```
CAGTGATAAT TTCTGGGTTA AGGCAATAGC AATATTTCTG CATATAAATA TTTCTGCATA      1821

TAAATTGTAA CTGATGTAAG AGGTTTCATA TTGCTAATAG CAGCTACAAT CCAGCTACCA      1881

TTCTGCTTTT ATTTTATGGT TGGGATAAGG CTGGATTATT CTGAGTCCAA GCTAGGCCCT      1941

TTTGCTAATC ATGTTCATAC CTCTTATCTT CCTCCCACAG CTC CTG GGC AAC GTG       1996
                                             Leu Leu Gly Asn Val
                                                             110

CTG GTC TGT GTG CTG GCC CAT CAC TTT GGC AAA GAA TTC ACC CCA CCA        2044
Leu Val Cys Val Leu Ala His His Phe Gly Lys Glu Phe Thr Pro Pro
            115                 120                 125

GTG CAG GCT GCC TAT CAG AAA GTG GTG GCT GGT GTG GCT AAT GCC CTG        2092
Val Gln Ala Ala Tyr Gln Lys Val Val Ala Gly Val Ala Asn Ala Leu
            130                 135                 140

GCC CAC AAG TAT CAC TAAGCTCGCT TCTTGCTGT CCAATTTCTA TTAAAGGTTC         2147
Ala His Lys Tyr His
            145
```

CTTTGTTCCC TAAGTCCAAC TACTAAACTG GGGGATATTA TGAAGGGCCT TGAGCATCTG      2207

GATTCTGCCT AATAAAAAAC ATTTATTTTC ATTGCAATGA TGTATTTAAA TTATTTCTGA      2267

ATATTTTACT AAAAAGGGAA TGTGGGAGGT CAGTGCATTT AAAACATAAA GAAATGAAGA      2327

GCTAGTTCAA ACCTTGGGAA AATACACTAT ATCTTAAACT CCATGAAAGA AGGTGAGGCT      2387

GCAAACAGCT AATGCACATT GGCAACAGCC CTGATGCCTA TGCCTTATTC ATCCCTCAGA      2447

AAAGGATTCA AGTAGAGGCT TGATTTGGAG GTTAAAGTTT TGCTATGCTG TAT             2500

(2) INFORMATION FOR SEQ ID NO:11:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO:11:

```
Met Val His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
                20                  25                  30

Leu Val Val Tyr Pro Trp Thr Gln Arg Phe Phe Glu Ser Phe Gly Asp
             35                  40                  45

Leu Ser Thr Pro Asp Ala Val Met Gly Asn Pro Lys Val Lys Ala His
         50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                 85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
            115                 120                 125

Ala Ala Tyr Gln Lys Val Val Ala Gly Val Ala Asn Ala Leu Ala His
            130                 135                 140

Lys Tyr His
145
```

(2) INFORMATION FOR SEQ ID NO:12:

(i) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

GGGATTACAG CGTGAGCCAA    20

(2) INFORMATION FOR SEQ ID NO:13:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

GAGGAAGGAA GGGGTGGACT    20

DETECTION OF HUMAN α-THALASSEMIA MUTATIONS AND THEIR USE AS PREDICTORS OF BLOOD-RELATED DISORDERS

BACKGROUND OF THE INVENTION

A. Field of the Invention

The present invention relates in general to a method and to a kit of materials for performing assays for blood-related disorders, and more particularly to a method and kit for predicting whether a human subject has a mild α-thalassemia genotype, and whether a human subject will develop hypertension.

B. Background

The modern development of molecular biological techniques has permitted investigation into the genetic abnormalities that cause, or correlate with, specific human disease states and conditions. For example, restriction fragment length polymorphism (RFLP) analysis facilitates the identification of genetic defects which cause or are correlated with disease states, and facilitates the identification of individuals possessing the genetic defects. RFLP procedures involve digesting DNA with one or more restriction enzymes and analyzing the restriction fragments using, e.g., Southern blot hybridizations employing selected gene probes. See Alberts et al., *Molecular Biology of the Cell*, Second Edition, New York: Garland Publishing (1989), pp. 270–71.

The polymerase chain reaction (PCR) and its many variations are particularly useful tools for investigation into genetic abnormalities that underlie disease states and conditions. (See, e.g., Erlich et al., *Current Communications in Molecular Biology: Polymerase Chain Reaction*, Cold Spring Harbor: Cold Spring Harbor Press (1989); Innis et al., *PCR Protocols: A Guide to Methods and Applications*. San Diego: Academic Press (1990).) PCR is used to amplify a DNA or one or more portions thereof that are of particular interest, to facilitate further characterization of the amplified portion. Such further characterization includes gel electrophoresis to determine size, nucleotide sequencing, hybridization studies using particular probes, and the like. See generally, Sambrook et al., *Molecular Cloning—A Laboratory Manual*, Second Edition, Cold Spring Harbor: Cold Spring Harbor Press (1989).

When a genetic abnormality has been correlated with a physiological condition or disease state, Northern and Southern hybridization techniques [see Sambrook et al. (1989), chapters 7 and 9] with a specific oligonucleotide probe permit the determination of whether the genetic abnormality is present or absent in a particular individual's genome. Nucleotide sequencing techniques may be used to confirm that a particular individual possesses or lacks a particular known genetic trait. See, e.g., Sambrook et al., Chapter 13; Drmanac et al, *Science*, 260:1649–52 (1993); Mirzabekov, *TIBTECH*, 12:27–32 (1994); Innis et al., U.S. Pat. No. 5,075,216.

Hemoglobin is a complex, iron-containing, allosteric erythrocyte protein that carries oxygen from the lungs to cells and carbon dioxide from cells to the lungs. Hemoglobin A, the principle adult hemoglobin protein, comprises four polypeptide chains (two α-globin chains and two β-globin chains) and is among the best characterized of human proteins. *Human Hemoglobins*, H. F. Bunn, B. G. Forget, and H. M. Ranney (Eds.), Philadelphia: W. B. Saunders Co., (1977). A number of human disease states have been attributed to genetic mutations effecting one or more of the genes encoding hemoglobin polypeptide chains, including sickle cell anemia, which results from a point mutation in the hemoglobin β-chain. Alpha- and beta-thalassemia conditions are blood-related disorders which result from genetic mutations manifested phenotypically by deficient synthesis of one type of globin chain, resulting in excess synthesis of the other type of globin chain. See generally Weatherall et al., *The Thalassaemia Sndromes*, 3rd ed., Oxford, Blackwell Scientific, 1981.

Alpha-thalassemia and its associated clinical syndromes can result from either a deletion or a point mutation effecting one or both α-globin genes (or gene controlling sequences) that results in reduced synthesis of hemoglobin alpha-chains. The resultant imbalance between α and β chain production leads to accumulation of excess β chains that are unstable and precipitate within the cell, altering the cell membrane and causing the clinical manifestations. Higgs, Q. *J. Med.* 86:559–64 (1993); Schrier and Mohandas, *Blood*, 79:1586–92 (1992). Greater than 95% of α-thalassemia conditions are caused by deletions of one or more α-globin genes, whereas structural mutations only rarely cause a thalassemic syndrome. Kazazian, *Semin. Hematol.*, 27:209–28 (1990); Embury et al., *J. Clin. Invest.*, 66:1319–25 (1980).

In a normal individual, two α-globin genes along with three other pseudogenes ($\psi\zeta_1$, $\psi\alpha_2$, and $\psi\alpha_1$) and a gene of undetermined function ($\theta_1$) are all located on the short arm of chromosome 16 in the order: telomere-$\psi\zeta_1$-$\psi\alpha_2$-$\psi\alpha_1$-$\alpha_2$-$\alpha_1$-$\theta_1$-centromere. See generally, Higgs et al., *Blood*, 73:1081–104 (1989). Thus, a normal individual (genotype αα/αα) possesses four α-globin genes: two on each chromosome 16.

The mild α-thalassemia genotype—deletion of one of the four α-globin genes—is one of the most common genetic abnormalities in the world. Kan, *JAMAE*, 267:1532–6 (1992); Baysal and Huisman, *Am. J. Hematol*, 46:208–13 (1994); Liebhaber, *Hemoglobin*, 13:685–731 (1989). Among black Americans, this condition occurs with a prevalence of 27.5% (Dozy et al., *Nature*, 280:605–7 (1979)), representing a gene frequency of 0.16, and suggesting that over 8 million black Americans could be affected by this condition.

The majority of these single alpha gene deletions are characterized by a ~3.7 kilobase (kb) deletion ($-\alpha^{3.7}$; "rightward deletion") within the α gene locus as depicted in FIG. 1. Embury et al. (1980); Higgs et al. (1989). Three subclasses of the $-\alpha^{3.7}$ deletion (FIG. 1, $-\alpha^{3.7i}$, $-\alpha^{3.7ii}$, $-\alpha^{3.7iii}$) have been detected by Southern blot hybridization. Higgs et al., *Nucleic Acids Res.*, 12:6965–77 (1984). In all three classes, the 3.7 kb deletion results in a single, hybrid, functional α gene consisting of a 5' $\alpha_2$ sequence and a 3' $\alpha_1$ sequence. The genotype of a heterozygous individual inheriting one $-\alpha^{3.7}$ and one normal chromosome 16 may be expressed as $-\alpha^{3.7}\alpha/\alpha\alpha$. A "leftward deletion," resulting in the loss of a 4.2 kb segment containing the $\alpha_2$ locus ($-\alpha^{4.2}$) also has been characterized. (See FIG. 1.) The $-\alpha^{4.2}\alpha/\alpha\alpha$ genotype is rare in the overall U.S. population (Higgs et al. (1989)), but can be prevalent in 58% of some Chinese populations. Baysal and Huisman (1994).

If an α-globin gene deletion is present on both of an individual's chromosomes, a clinically observable thalassemia occurs (α-thalassemia trait). This genotype occurs with an incidence of almost 3% in American blacks. Dozy et al. (1979). It is, therefore, likely to be a significant cause of microcytic anemia that does not respond to oral iron therapy in black children. Kazazian (1990).

In individuals from Southeast Asia and the Mediterranean areas, the most common deletions involve both α genes on the same chromosome 16 (FIG. 1: --SEA or --MED). The prevalence of the --SEA mutation is 3–5% in Southeast Asia. Bowden et al., *Br. J. Haematol,* 81:104–8 (1992). The prevalence of the --MED deletion is less than 1% in the Mediterranean basin. Id. Several other a gene deletions have been characterized. See, e.g., Higgs et al. (1989); Baysal and Huisman (1994). Inheritance of double deletions on both chromosomes (e.g. --SEA/--SEA) results in no α-chain production, and such fetuses often die in utero. If three of an individual's α-gene loci are deleted (e.g., $-\alpha^{3.7}\alpha/\text{--SEA}$), severe thalassemia occurs (hemoglobin H disease).

Since most α-thalassemia mutations are due to deletions of one or more α-loci on chromosome 16 Kazazian (1990), supra; Embury et al. (1980), supra), specific PCR-based molecular biological techniques to detect these deletions (versus non-deletional mutations) have been developed. See, e.g., Baysal and Huisman (1994), supra; Bowden et al. (1992), supra; Dode et al., *Br. J. Haematol.,* 76:275–81 (1990); Lebo et al., *Hum. Genet.,* 85:293–9 (1990); Lundeberg et al., *Biotechniques,* 10:68–75 (1991); all incorporated by reference in their entirety. While these methods take advantage of the sensitivity of polymerase chain reaction (PCR) techniques, some (Dode et al. (1990); Lebo et al. (1990)) require the use of restriction enzyme cleavage of the amplified product, prior to analysis, for adequate interpretation. In addition, none of these methods attempt to reliably and objectively distinguish between homozygotes, heterozygotes, and normals by using quantitative PCR techniques. See Lundeberg et al. (1991); Lubin et al., *Mol. Cell. Probes,* 5:307–17 (1991). Improved techniques are needed for detecting α-globin gene mutations rapidly and inexpensively, and for reliably distinguishing between various α-globin genotypes.

Hypertension (high blood pressure), a prevalent and chronic cardiovascular disorder, comprises a significant risk factor for cardiovascular disease generally, and more particularly for coronary artery disease, heart failure, kidney failure, stroke, and other conditions that, collectively, afflict millions of people and consume vast amounts of society's health care resources. An estimated 15–20% of the adult population of the United States and other industrialized nations are afflicted with hypertension. See James and Baker, "Human Population Biology and Blood Pressure: Evolutionary and Ecological Considerations and Interpretations of Population Studies," in *Hypertension: Pathophysiology, Diagnosis, and Management. Second Edition,* Laragh and Brenner (eds.), New York: Raven Press, Ltd., Chapter 8 (1995).

Hypertension in certain subpopulations is even more widespread and problematic than in the population as a whole. High blood pressure is the major health problem in most black populations in the Western Hemisphere and is emerging as a major problem in many urban areas of Africa. See *generally* Grim et al., "High Blood Pressure in Blacks: Salt, Slavery, Survival, Stress, and Racism," in *Hypertension: Pathophysiology, Diagnosis, and Management. Second Edition,* Laragh and Brenner (eds.), New York: Raven Press, Ltd., Chapter 12 (1995). The prevalence of hypertension in African Americans is the highest in the world. Id. Various hypotheses have been advanced to explain the prevalence of hypertension in African Americans, including the evolution of a salt-conserving genotype and the stress of living in a racist society. Id.

Increasingly, individuals who are made aware of the health risks associated hypertension are able to take steps to manage their blood pressure, including lifestyle management choices (e.g., dietary choices, weight management, exercise, consumption of alcohol and tobacco). Unfortunately, hypertension generally is asymptomatic until complications develop. Consequently, many undiagnosed individuals exist who are unaware of the beneficial blood pressure management regimens in which they can engage. A long felt need exists to better identify individuals at risk for developing hypertension, so that such individuals may counseled as to lifestyle regimens which reduce the likelihood of the development of hypertension, and so that such individuals may act to monitor themselves more closely for the development of hypertension. Although certain known factors predispose individuals to hypertension (family history, weight), a long felt need exists for markers which identify individuals having a predisposition for hypertension.

For some hypertensive patients, physicians are able to diagnose an underlying causative factor for the high blood pressure and treat the patients with the most appropriate treatment regimen. However, the vast majority of hypertensive patients suffer from "primary" (essential) hypertension, where physicians are unable to identify a particular cause for hypertension. A long felt need exists to identify causative factors for hypertension in individuals, to permit physicians to prescribe the most effective treatment regimens having the fewest side-effects, and to permit the development of new treatments tailored to the particular causative factors.

Notwithstanding the availability of promising investigative tools such as PCR, progress in the identification of genetic markers for hypertension has been reported to be slow, and to likely be a long time in coming, due to the at least 274 genes that appear to have major influences on physiological control systems that lead to increases in blood pressure, blood sugar, obesity, and cholesterol. Grim et al., supra, p. 182; Leckie, *BioEssays,* 14(1):37–41 (1992).

SUMMARY OF THE INVENTION

The present invention solves one or more of the aforementioned needs by identifying a genetic marker useful for predicting the development of certain blood-related disorders, including hypertension, by providing a method of screening a human subject for an increased potential (i.e., a risk) of developing a blood-related disorder, and by providing an apparatus/kit for screening a human subject for an increased potential of developing a blood-related disorder. The genetic marker can be used alone or in combination with other genetic markers for predicting the development of a blood-related disorder. In a related aspect, the invention provides an improved method for determining a human subject's genotype with respect to a particular gene locus (i.e., the α-globin gene locus on human chromosome 16).

The invention is based on the discovery that adults having a genotype comprising a hemoglobin α-gene deletion are significantly more likely to be hypertensive than adults having a normal (αα/αα) gentoype. Thus, in one aspect the invention provides a method of screening a human subject for a risk of developing a blood-related disorder comprising the steps of: (a) assaying genomic DNA of a human subject to determine a presence or an absence of an α-globin mutation; and (b) correlating the presence of an α-globin mutation in the genomic DNA to a risk of developing a blood-related disorder. In a preferred embodiment, the method screens a human subject for a risk of developing hypertension, stroke, myocardial infarction, diabetes, hemochromatosis, and/or preeclampsia/eclampsia conditions. More preferably, the blood-related disorder is hypertension, stroke, myocardial infarction, diabetes, and/or hemochromatosis. Most preferably, the method screens a normotensive human subject for hypertension.

A person (e.g., a medical practitioner or other health care practitioner) can estimate a probability that any particular individual will develop a blood-related disorder, basing the estimate upon, e.g., the prevalence of the disorder in the general population or the individual's ethnic population, the individual's sex and age, and the like. In the present method, the phrase "screening a human subject for 'a risk' of developing a blood-related disorder" means screening a human subject for the presence or absence of a genetic marker (i.e., an α-globin mutation), the presence of which correlates with a greater likelihood (i.e., probability) of developing the blood-related disorder than would otherwise be predicted (e.g., from the prevalence of the disorder in the general population or in the subject's ethnic population, the subject's sex and age, and the like).

By "genomic DNA" is meant DNA from the human subject containing at least the portion of chromosome 16 wherein the human α-globin genes have been mapped. In a preferred embodiment, genomic DNA is isolated from a sample of the subject's somatic cells (e.g., blood cells).

By "an α-globin mutation" is meant any genetic mutation affecting transcription or translation of the α-genes of chromosome 16 that results in reduced synthesis of normal α-globin chains, relative to the number of α-globin chains synthesized in a normal (αα/ααgenotype) human subject. In a preferred method, the subject's genomic DNA is assayed to determine a presence or an absence of an α-globin deletion mutation. More preferably, the genomic DNA is assayed to determine a presence or an absence of an α-globin deletion mutation selected from the group consisting of an $-\alpha^{3.7}$ deletion, an --MED deletion, an --SEA deletion, an $-\alpha^{4.2}$ deletion, and an --BRIT deletion. Of particular interest is a method of assaying the genomic DNA to determine a presence or an absence of an $-\alpha^{3.7}$ deletion mutation, since such mutations are prevalent in, e.g., black American populations. It has been discovered that the presence of an $-\alpha^{3.7}$ deletion correlates to a risk of developing hypertension even when the human subject is heterozygous for an $-\alpha^{3.7}$ deletion (e.g., $\alpha\alpha/-\alpha^{3.7}\alpha$) and is free from clinical manifestations of an α-thalassemia condition.

In another aspect, the invention comprises a method of determining an increased potential for developing hypertension in a normotensive human individual comprising the steps of: (a) isolating DNA from the human individual; (b) assaying the DNA for the presence of a deletion relative to DNA of a normal human subject, the deletion comprising a reduction in the number of α-globin genes in the genome of the normotensive human individual; and (c) determining a potential for developing hypertension in the normotensive human individual, wherein the presence of the deletion in the DNA isolated from the normotensive human individual is indicative of an increased potential for developing hypertension. By "normotensive human individual" is meant a person whom a physician would not diagnose as hypertensive.

By "increased potential for developing hypertension" is meant a greater likelihood (probability) of developing hypertension than would be predicted (statistically) based solely upon an individual's other traits known to influence blood pressure (e.g., the individual's age, sex, ethnicity, and the like). According to the method of the invention, if a deletion comprising a reduction in the number of α-globin genes is present in the DNA of a normotensive human individual, the individual is determined to have an increased potential for developing hypertension. By "reduction in the number of α-globin genes" is meant a deletion which results in the human individual having fewer than the four functional α-globin genes of a normal human subject.

In a preferred embodiment of the method, the DNA is assayed for the presence of a deletion of at least about 3.7 kilobases of DNA. Prevalent α-globin deletion mutations such as the $-\alpha^{3.7}$ deletion mutation, the $-\alpha^{4.2}$ deletion mutation, the --SEA deletion mutation, and the --MED deletion mutation are deletions of at least about 3.7 kb and are deletions which comprise a reduction (by one or two genes) in the number of α-globin genes in the genome, relative to the genome of a normal human subject (αα/αα)

The skilled artisan understands that numerous molecular biological techniques may be employed to assay DNA for the presence of a deletion, particularly when the relevant portion of the human genome has been characterized extensively (as is the case for the region of chromosome 16 containing α-globin genes, for which a nucleotide sequence has been determined). Thus, in one embodiment, DNA is assayed for the presence of a deletion by determining a partial nucleotide sequence of the subject's DNA, the partial nucleotide sequence indicating the presence or absence of the deletion. In an alternative embodiment, DNA is assayed for the presence of a deletion by performing a restriction endonuclease digestion of the subject's DNA and a Southern hybridization analysis of the restriction-digested DNA, the Southern hybridization indicating the presence or absence of the deletion. In a preferred embodiment, DNA is assayed for the presence of a deletion by performing a multiplex polymerase chain reaction as described herein in detail.

Thus, in a related aspect, the invention comprises a method for determining an increased potential for developing hypertension in a human individual comprising the steps of: (a) isolating genomic DNA from the human individual; (b) performing a multiplex polymerase chain reaction with the genomic DNA to amplify a marker portion and a control portion thereof, wherein the presence of an α-globin gene deletion in the genomic DNA reduces the quantity of marker amplicons produced in the multiplex polymerase chain reaction relative to the quantity of control amplicons produced in said multiplex polymerase chain reaction; and (c) determining a potential for developing hypertension from the quantity of marker amplicons relative to the quantity of control amplicons.

More particularly, the invention comprises a method for determining an increased potential for developing hypertension in a human individual comprising the steps of: (a) isolating genomic DNA from the human individual; (b) performing a multiplex polymerase chain reaction with the genomic DNA to amplify a marker portion and a control portion thereof, wherein the presence of an α-globin gene deletion in the genomic DNA reduces the quantity of marker amplicons produced in the multiplex polymerase chain reaction relative to the quantity of control amplicons produced in the multiplex polymerase chain reaction; (c) determining a ratio of marker amplicons to control amplicons produced in the multiplex polymerase chain reaction; and (d) comparing the ratio of step (c) to a ratio of marker amplicons to control amplicons produced in a multiplex polymerase chain reaction performed with genomic DNA of a normal human subject, wherein a lower marker amplicon to control amplicon ratio of step (c) indicates an increased potential for developing hypertension.

As described in detail herein, a multiplex polymerase chain reaction is a polymerase chain reaction wherein more than one region (segment) of template DNA is amplified simultaneously in a single reaction vessel. The amplification of more than one region of template DNA is achieved through the use of more than one pair of PCR primers, each pair of primers designed to amplify a single region of template DNA. An "amplicon" is a discreet amplification product synthesized in the M-PCR reaction and corresponding to one of the regions that is intended to be amplified.

By "marker portion" of genomic DNA is meant a segment of genomic DNA (on chromosome 16 ) that is amplified in the M-PCR reaction unless an α-globin gene deletion is present, in which case no amplification of the segment occurs. Human individuals possess two chromosomes 16, either or both of which may have an α-globin gene deletion. By "control portion" of genomic DNA is meant a segment of genomic DNA that is amplified in the M-PCR reaction irrespective of whether an α-globin gene deletion is present on one or both of an individual's two chromosomes 16. Thus, the presence of an α-globin gene deletion in an individual's genomic DNA reduces the quantity of marker amplicons produced in the multiplex polymerase chain reaction relative to the quantity of control amplicons produced in the multiplex polymerase chain reaction. The quantity of marker amplicons produced is reduced to essentially zero if both of an individual's chromosomes 16 contain the deletion.

In a preferred embodiment of the method, the step of performing a multiplex polymerase chain reaction includes the step of preparing a polymerase chain reaction solution, the solution comprising genomic DNA isolated from the human individual, a first pair of oligonucleotide primers for amplifying the marker portion of the DNA, and a second pair of oligonucleotide primers for amplifying the control portion of the DNA. Generally, the polymerase chain reaction solution further contains a PCR buffer, dNTP's (dATP, dGTP, dCTP, and dTTP), and a thermostable DNA polymerase enzyme. Optionally, the polymerase chain reaction solution contains more than two pairs of oligonucleotide primers (e.g., a solution may contain a third pair of primers, for amplifying a second marker portion of the DNA). A preferred pair of primers for amplifying a marker portion of DNA are primers F37.1F and F37.3, having the nucleotide sequences in SEQ ID NO: 4 and 5, respectively. A preferred pair of primers for amplifying a control portion of DNA are primers GH20F and PCO4, having the nucleotide sequences in SEQ ID NO: 8 and 9, respectively.

It will be apparent from the teachings herein that when M-PCR is performed using a particular first pair of primers and a particular second pair of primers, then a characteristic ratio of marker amplicons to control amplicons will result for template DNA isolated from a normal human subject (genotype αα/αα). A characteristic, statistically-significant lower ratio will result for template DNA isolated from a heterozygous human individual having one normal chromosome 16 (αα) and one chromosome 16 having an α-globin gene deletion. For example, using the preferred pairs of primers described in the preceding paragraph in a series of replicate M-PCR reactions, the intra-run peak ratios (mean ±standard deviation) in normal human subjects was 0.790±0.081 (n=6). The intra-run mean for $-\alpha^{3.7}$ deletion heterozygotes was 0.191±0.026 (n=7). In the between-run replicate analysis (5 runs over 8 weeks at 1–2 week intervals), the ratio in normals was 0.879±0.163 (n=5), and in $-\alpha^{3.7}$ heterozygotes was 0.217±0.059 (n=5).

It will further be apparent that a number of discrete "cut-off" ratios may be selected statistically to distinguish between "normals" and "heterozygotes" with a desired sensitivity, specificity, positive predictive value, and/or negative predictive value. Selection of a cut-off is within the ordinary skill of the art using routine statistical analysis. For the preferred pairs of primers described above, a preferred cut-off ratio of is a ratio that is about two standard deviations below (lower than) the characteristic ratio for normal human subjects, i.e., a ratio of about 0.6.

In a preferred embodiment, the method further comprises isolating genomic DNA from a normal human being; performing a control multiplex polymerase chain reaction with the genomic DNA of the normal human being to amplify a marker portion and a control portion thereof; and determining a ratio of marker amplicons to control amplicons produced in the control multiplex polymerase chain reaction; wherein in step (d), a lower marker amplicon to control amplicon ratio for the human individual compared to the normal human being indicates an increased potential for developing hypertension. The performance of these additional steps provides an "intra-run" ratio of marker amplicons to control amplicons for a normal human subject, for comparison to the ratio of amplicons determined for the human individual being tested. It is believed that the determination of such an "intra-run" ratio provides optimum accuracy in the method of the invention.

In a related aspect, the invention provides a genetic counseling method comprising the steps of: (a) isolating genomic DNA from a human individual; (b) assaying the DNA for a deletion relative to DNA of a normal human subject, the deletion reducing the number of α-globin genes in the genome of the human individual; (c) determining a potential for developing a blood-related disorder in the human individual, wherein the presence of the deletion in the genomic DNA of the human individual is indicative of an increased potential for developing the blood-related disorder, the blood-related disorder selected from the group consisting of hypertension, stroke, myocardial infarction, diabetes, hemochromatosis, a preeclampsia condition, and eclampsia; and (d) advising the human individual with respect to the individual's potential for developing the blood-related disorder. By "advising" the human individual is meant, e.g., providing the individual with the assay results and with the interpretation of those results (i.e., either normal or an increased potential for developing the blood-related disorder). In a preferred embodiment, the blood-related disorder is hypertension, stroke, myocardial infarction and/or diabetes. In a more preferred embodiment, the blood-related disorder is hypertension.

In another related aspect, the invention provides a method of determining a hypertension-correlated genetic disorder in a hypertensive human individual comprising the steps of: (a) isolating DNA from the human individual; (b) assaying the DNA for a deletion relative to DNA of a normal human subject, the deletion comprising a reduction in the number of α-globin genes in the genome of the hypertensive human individual; and (c) determining a presence of a hypertension-correlated genetic disorder in the individual from a presence of the deletion in the DNA. The determination of a hypertension-correlated genetic disorder in an individual facilitates a determination of the optimum hypertension treatment regimen for the individual.

In another aspect, the invention provides a kit for screening a human subject for an increased potential of developing a blood-related disorder, the kit comprising: an assay means for assaying a sample of genomic DNA from a human subject for the presence of an α-globin mutation, wherein the assay means produces a positive α-globin assay result if the α-globin mutation is present in the DNA of the subject, and the assay means produces a negative assay result if the DNA of the subject is free of the α-globin mutation; and a means for correlating a positive α-globin assay result to an increased potential of developing a blood-related disorder, the disorder selected from the group consisting of hypertension, stroke, myocardial infarction, diabetes, hemochromatosis, a preeclampsia condition, and eclampsia.

Exemplary assay means include materials for performing molecular biological techniques to determine the presence of an α-globin gene mutation. Thus, the assay means may include DNA sequencing materials, PCR materials, restriction digestion/southern hybridization materials, and combinations thereof. In a preferred embodiment, the assay means includes M-PCR materials. For example, the assay means comprises a pair of α-globin deletion-sensitive oligonucleotide primers. The assay means may further include other materials to facilitate multiplex PCR analysis as described herein. Preferably, the assay means further comprises first and second samples of human genomic DNA, the first sample having a homozygous normal α-globin genotype, the second sample having a heterozygous α/αα-globin-deletion genotype (e.g., an αα/-$\alpha^{3.7}\alpha$ genotype).

By a means for correlating a positive α-globin assay result to an increased potential of developing a blood-related disorder is meant a chart, table, graph, text, or other reference that permits a medical practitioner to correlate assay results for a particular human subject to statistical risk for developing a particular blood-related disorder. For example, the chart, table, graph, or text is based on assay data disclosed herein, or upon further assay data obtained according to the teachings herein. The chart, table, graph, or text, or the data contained therein, may be provided in computer-readable form (e.g., on a floppy disc or compact disc).

In yet another aspect, the invention provides a method for assaying for a mild α-thalassemia genotype in a human individual comprising the steps of: (a) isolating genomic DNA from the human individual; (b) performing a multiplex polymerase chain reaction with the genomic DNA to amplify a marker portion and a control portion thereof, wherein the presence of an α-globin gene deletion in the genomic DNA reduces the quantity of marker amplicons produced in the multiplex polymerase chain reaction relative to the quantity of control amplicons produced in the multiplex polymerase chain reaction; (c) determining a ratio of marker amplicons to control amplicons produced in the multiplex polymerase chain reaction; and (d) comparing the ratio of step (c) to a ratio of marker amplicons to control amplicons produced in a multiplex polymerase chain reaction performed with genomic DNA of a normal human subject, wherein a mild α-thalassemia genotype in the individual correlates with a lower marker amplicon to control amplicon ratio of step (c) compared to the ratio of marker amplicons to control amplicons produced in a multiplex polymerase chain reaction performed with genomic DNA of a normal human subject. Multiplex PCR as taught herein provides a characteristic ratio of marker amplicons to control amplicons for template DNA isolated from a normal human genotype; a characteristic, statistically-significant lower ratio for template DNA isolated from a heterozygote individual having one chromosome with the deletion and one chromosome without the deletion, and a ratio near zero for template DNA isolated from an individual having the deletion on both chromosomes. In preferred embodiments, the method of the invention is an assay for the presence of a -$\alpha^{3.7}\alpha$/αα genotype in a human individual. For example, a pair of M-PCR primers is employed in the M-PCR reaction to amplify a marker portion of genomic DNA that is absent from a chromosome 16 having an -$\alpha^{3.7}$ deletion. A second pair of primers is employed to amplify a control portion of genomic DNA. Preferably, a third pair of primers also is employed to amplify a portion of genomic DNA that is present in a chromosome 16 having a -$\alpha^{3.7}$ deletion but absent from a chromosome 16 having an --SEA, an --MED, or a --BRIT deletion. In another preferred embodiment, the method of the invention is an assay for the presence of a -$\alpha^{4.2}\alpha$/αα genotype in a human individual.

In a related aspect, the invention provides a kit for determining the α-globin genotype of a human individual comprising, in association, a first pair of oligonucleotide primers for amplifying a first marker portion of a human chromosome 16, the first marker portion being absent from a human chromosome 16 having a single α-gene deletion selected from the group consisting of an -$\alpha^{3.7}$ deletion and a -$\alpha^{4.2}$ deletion; a second pair of oligonucleotide primers for amplifying a second marker portion of a human chromosome 16, the second marker portion being present in a human chromosome 16 having the single α-gene deletion and being absent from a human chromosome 16 having an --MED deletion; and a control pair of oligonucleotide primers for amplifying a control portion of human genomic DNA. In one embodiment, the single α-gene deletion is an -$\alpha^{3.7}$ deletion. A preferred first pair of oligonucleotide primers in this embodiment have the nucleotide sequences set forth in SEQ ID NO: 4 and 5. In another embodiment, the single α-gene deletion is an -$\alpha^{4.2}$ deletion. A preferred first pair of oligonucleotide primers in this embodiment have the nucleotide sequences set forth in SEQ ID NO: 12 and 13. In either of the aforementioned embodiments, a preferred second pair of oligonucleotide primers have the nucleotide sequences set forth in SEQ ID NO: 6 and 7. By "control portion" of genomic DNA is meant a segment of genomic DNA that is amplified in an M-PCR reaction irrespective of whether an α-globin gene deletion is present on one or both of an individual's two chromosomes 16. A preferred control pair of oligonucleotide primers have the nucleotide sequences set forth in SEQ ID NO: 8 and 9. The kit may further include other materials to facilitate multiplex polymerase chain reaction analysis as described herein. Such other materials include, for example, a PCR buffer, dNTPs, a thermostable DNA polymerase, a sample of genomic DNA having a homozygous normal α-globin genotype, a sample of genomic DNA having a heterozygous αα/α-globin-deletion genotype (e.g., a αα/-$\alpha^{3.7}\alpha$ genotype or a αα/-$\alpha^{4.2}\alpha$ genotype), combinations of such materials, and the like.

Numerous other aspects and advantages of the present invention will be apparent upon the following detailed description thereof, reference being made to the drawing wherein:

DETAILED DESCRIPTION

Figure 1:
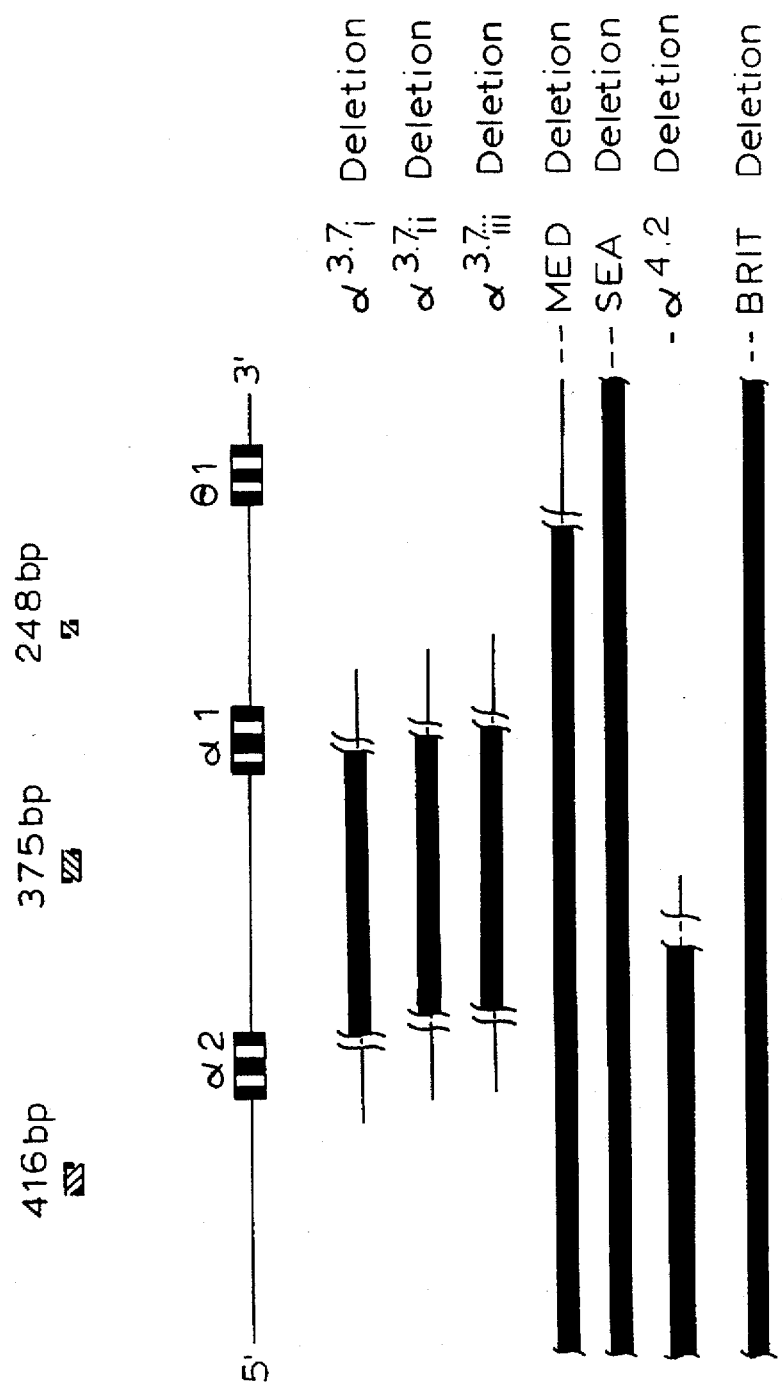
FIG. 1 is a partial map of a portion of chromosome 16 (top line), depicting the relationship between the genes which encode the alpha globin polypeptide chains (α1 and α2), common α-globin gene deletions, and the deletion-sensitive primer binding regions. Each alpha gene has three exons (top line, black bars) separated by two introns (white bars). The location of common α-globin deletion mutations (-$\alpha^{3.7}$ (three subclasses); --MED; --SEA; -$\alpha^{4.2}$; and --BRIT) are depicted as thick black bars below the line depicting chromosome 16. The dashed lines at the ends of the black bars indicate the region in which cross-over occurs, resulting in heterogeneity with regard to the exact length of these deletions. The three related -$\alpha^{3.7}$ deletions are depicted, each of which results in a single hybrid a gene composed of a 5' α2 sequence and a 3' α1 sequence. The cross-hatched boxes (above the line depicting the α-globin genes on chromosome 16 ) represent the location of amplification products (amplicons) resulting from the binding of deletion-sensitive PCR primers. The numbers above the amplicons represent the length of the amplified product in base pairs.

The present invention is based upon the discovery that adult subjects having a genotype comprising an α-globin deletion, including subjects having a "silent carrier" α-thalassemia genotype wherein only one of the four α-globin genes is deleted (e.g., –α$^{3.7}$α/αα genotype), are significantly more likely to suffer from hypertension than "normal" subjects (αα/αα genotype).

With reference to a particular human subject, a diagnosis of "hypertension" means that the subject has a blood pressure that is higher, to a clinically significant extent, than would be expected for a typical human subject of the same sex and age as the particular subject. Such a diagnosis is within the routine skill of a subject's medical practitioner, notwithstanding the fact that blood pressure (like height, weight, and other physical characteristics) is a continuous variable in a given population. A diastolic blood pressure greater than 95 mm Hg was selected to define hypertension for some human subjects in the Examples herein.

The absence (deletion) of one or more α-globin genes in a subject's genome results in the synthesis of fewer than the optimum quantity of hemoglobin α-chains, resulting in the existence of excess hemoglobin β-chains in the subject's erythrocytes. See, e.g., Kazazian (1990), supra; Higgs et al. (1989), supra. Without intending to be limited to a particular theory of the invention, it is believed that the excess β-chains increase the viscosity of the subject's blood relative to the blood of non-carriers (persons having a normal α-globin genotype), perhaps by increasing erythrocyte cell membrane rigidity. Compare Crowley et al., Annals Clin. Lab. Sci., 22(4):229–35 (1992), reporting increased blood viscosity in β thalassemic subjects relative to healthy subjects having similar hematocrit levels. The increased blood viscosity, in turn, contributes to hypertension.

Alternatively, it is believed that the presence of free hemoglobin in individuals having an α-globin deletion genotype contributes to hypertension by binding nitric oxide (a natural vasodilator), thereby inhibiting normal vasodilation. More particularly, the excess hemoglobin β-chains in the erythrocytes of these individuals form β-chain tetramers which precipitate within the erythrocytes. The interaction between these excess β-chains and the erythrocyte membrane is believed to cause hemoglobin leakage from the erythrocytes into the plasma. More significantly, the excess β-chains in circulating erythrocytes are believed to alter the erythrocyte membrane itself (e.g., altering membrane rigidity). The altered erythrocytes are more readily destroyed in the spleen, and much of the hemoglobin from these destroyed cells is released into the lymphatic system. The increased plasma hemoglobin and, more significantly, the increased free hemoglobin in the lymph (which bathes the vascular endothelium) bind nitric oxide. The bound nitric oxide is thereby prevented from effecting vasodilation through interaction with the smooth muscles of blood vessel walls. In a related effect in the vascular compartment, the altered erythrocytes may adhere to endothelial surfaces more than normal erythrocytes, and hemoglobin in these adhering cells binds nitric oxide produced by the endothelial cells in close proximity. It is not believed that these theories are mutually exclusive.

Under the theory of the invention, it is believed that the physiological α-chain/β-chain imbalance associated with the mutation of a globin gene, and more particularly with a deletion mutation affecting an α-globin gene, predisposes a person to a number of additional blood-related disorders (in addition to hypertension) not previously correlated with mutations in globin genes generally or with mutations affecting α-globin genes in particular.

For example, an α-globin deletion genotype is believed to predispose an individual to a type of hemochromatosis, a disorder of iron metabolism characterized by excess deposition of iron in the tissues. Under the theory of the invention described above, the leakage of hemoglobin from erythrocytes (and/or the increased plasma and lymph concentrations of hemoglobin resulting from erythrocyte death and destruction) increase an individual's risk of iron overload from iron ingestion. Thus, an α-globin deletion genotype causes or predisposes an individual to develop a type of hemochromatosis.

An α-globin deletion genotype is believed to correlate with an increased likelihood that an individual will develop myocardial infarction or stroke. The increased blood viscosity and the reduced nitric oxide levels resulting from the damaged erythrocytes predispose individuals to develop a myocardial infarction or stroke. In the presence of atherosclerosis, the impact is even more dramatic since atherosclerotic plaques are also believed to bind nitric oxide. Since this further reduces the amount of nitric oxide available for dilatation of vascular smooth muscle, the presence of an α-globin deletion genotype may result in even earlier development of myocardial infarction or stroke.

An α-globin deletion genotype also is believed to predispose pregnant women to a preeclampsia condition—a toxemia of late pregnancy characterized by hypertension, edema, and proteinuria—and to eclampsia. Under the theory of the invention described above, erythrocyte adherence to the vascular endothelium and the increased plasma and lymph concentrations of hemoglobin resulting from erythrocyte death and destruction contribute to metabolic disturbances resulting in hypertension and other symptoms similar to those seen in preeclampsia, thereby predisposing an individual to develop a preeclampsia/eclampsia condition.

Similarly, an α-globin deletion genotype is believed to predispose individuals to diabetes and/or to increase their risk for early expression or more severe expression of diabetic symptoms.

The determination of whether a particular human subject has a genotype comprising an α-globin gene mutation, and especially an α-globin gene deletion, may be performed by any procedure known in the art for genotype characterizations. Such procedures include, for example, Southern hybridization procedures, Northern hybridization procedures, RFLP procedures, PCR procedures, DNA sequencing procedures, immunological, electrophoretic, and chromatographic procedures for detection of mutant polypeptides or β-chain tetramers, and other procedures. Many of the foregoing procedures generally involve an analysis of isolated genomic DNA from the human subject. Any known DNA isolation procedure may be employed. In a preferred embodiment, the genomic DNA is isolated from a blood sample taken from the subject.

In one preferred embodiment, a determination of the subject's genotype is performed with a DNA sequencing procedure, since such procedures are among the most definitive methods for determining a genotype. In a highly preferred embodiment, a polymerase chain reaction procedure is performed to determine a subject's genotype, such procedures being more rapid and cost-effective than DNA sequencing procedures. See, e.g., Baysal and Huisman (1994), supra. Optionally, a genotype determined with a PCR procedure is confirmed using a DNA sequencing procedure. Dode et al. (1990), supra, describes a method for characterizing α genes employing both PCR and sequencing. In a highly preferred embodiment, a human subject's genotype is determined after amplification of the affected region by a multiplex polymerase chain reaction (M-PCR) procedure as described herein. Optionally, the determination based upon analysis of the M-PCR reaction products is confirmed using a DNA sequencing procedure.

The present invention is further illustrated by the following examples. More particularly, Example 1 describes a multiplex polymerase chain reaction procedure for assaying (characterizing) the genomic DNA of an individual, to determine the presence or absence of a hemoglobin alpha-chain gene deletion in the individual's genome. Example 2 describes the use of the M-PCR procedure of Example 1 to demonstrate a correlation between a hemoglobin α-chain gene deletion and the blood-related disorder hypertension in adults, thereby demonstrating that the M-PCR procedure is useful for predicting a potential of a normotensive human subject for developing hypertension.

Example 3 describes a modification of the M-PCR procedure of Example 1 useful for detecting the presence of an $-\alpha^{4.2}$ deletion in an individual's genome. Example 4 is a prospective example which provides an M-PCR protocol for predicting a potential of a human subject for developing a blood-related disorder.

EXAMPLE 1

Detection of common α-globin gene deletions with multiplex PCR

The following procedure demonstrates a multiplex PCR procedure useful for determining the existence of an α-globin gene deletion in a subject's genome. The procedure also is described in detail in Bowie et al., "Detection of α-Thalassemias by Multiplex Polymerase Chain Reaction," Clin. Chem., 40(12):2260–66 (1994), incorporated herein by reference.

Isolation of Template DNA

DNA for use as PCR template DNA was isolated from the leukocytes of human subjects using a modification of the technique described by Lewin and Stewart-Haynes, Biotechniques, 13:522–3 (1992), incorporated herein by reference. EDTA-anticoagulated whole blood samples (10 μL) from clinical specimens collected for hematological analyses were hemolyzed with 500 μL of distilled water and centrifuged. The resultant pellet was washed twice with 500 μL of distilled water, resuspended in 10 μL of 0.2M KOH containing 0.05M dithiothrietol (DIT), and incubated at 65° C. for 5 minutes. Thereafter, 1 μL of 1.0M HCl was added. After mixing, 10 μL of 0.6M Tris-HCl, pH 8.3, containing 0.2M KCl was added. Finally, 20 μL of sterile distilled water was added and the solution was heated at 99.9° C. for 8 minutes to destroy any residual nucleases. DNA concentration was determined by absorbance measurements at 260 nm (1 absorbance unit=50 μg/ml of double-stranded DNA). DNA purity was assayed by absorbance measurements taken at 260 and 280 nm. While a 260 nm/280 m absorbance ratio of as low as 1.0 may be indicative of sufficient purity, it is preferred that template DNA be sufficiently pure to produce a 260/280 absorbance ratio of at least 1.6. It is contemplated that DNA isolated from any other cells (e.g., from tissue sample cells) is equally suitable for use as template DNA.

Primer synthesis

Primer sequences were selected using known characteristics of human α-globin genes, and oligonucleotide primers were synthesized for multiplex PCR as follows.

FIG. 1 presents a partial map of human chromosome 16, setting forth the relative positions of the α-globin genes and related gene locii. DNA sequence information for this region is known in the art [GENBANK locus HUMHBA4, "Human alpha globin psi-alpha-1, alpha-2 and alpha-1 genes, complete cds." Accessions J00153, J00079, J00154, J00155, J00156, K00418, X00168] and is set forth in SEQ ID NO: 1. The $\alpha_2$ and $\alpha_1$ polypeptide amino acid sequences are set forth in SEQ ID NO: 2 and 3, respectively. The regions of frequent gene deletions for the $\alpha_1$ and $\alpha_2$ locii also are depicted in FIG. 1. Based on the published DNA sequence for this region of chromosome 16, synthetic oligonucleotide primers were designed and synthesized to be complimentary to regions of human chromosome 16 affected by common α-globin gene deletions. More particularly, the nucleotide sequences of potential primer pairs were evaluated for maximum specificity, optimal GC content, and freedom from intramolecular structures using commercial software (OLIGO™, National Biosciences, Plymouth, Minn.). The primers were synthesized using the phosphoroamidite method on a DNA synthesizer (Gene Assembler Plus™, Pharmacia Biotechnology, Inc., Piscataway, N.J.), de-protected by treatment with concentrated ammonia for one hour at 55° C., passed through NAP 10 spin columns (Pharmacia Biotechnology, Inc.), and resuspended in de-ionized H$_2$O. The absorbances of primer solutions were read at 260 and 280 nm and diluted to an absorbance of 3.0 A (approximately 1.0 µmol/L).

Two primers were synthesized to amplify a 375 basepair (bp) region (FIG. 1) between the α$_1$ and α$_2$ genes of a normal chromosome 16 that is absent in a chromosome 16 harboring an –α$^{3.7}$ deletion, --SEA deletion, or --MED deletion:

| Primer F37.1F (SEQ ID NO: 4): | 5'-FACCATCCCCCCAAAAAACAT-3' |
|---|---|
| Primer F37.3 (SEQ ID NO: 5): | 5'-CTCTAACCATCACACAAGTA-3' |

Primer F37.1F is complimentary to the non-coding stand and corresponds to nucleotides 9166 to 9185 of SEQ ID NO: 1; Primer F37.3 is complimentary to nucleotides 9540 to 9521 of SEQ ID NO: 1.

A second pair of primers was synthesized to amplify a 248 bp region downstream from the α$_1$ gene of a normal chromosome 16. This 248 bp region also is present in a chromosome harboring a –α$^{3.7}$ deletion but absent from a chromosome harboring a --SEA deletion or a --MED deletion:

| Primer F13F (SEQ ID NO: 6): | 5'-FACTGGAGAGGAGAGCGGGGC-3' |
|---|---|
| Primer F14 (SEQ ID NO: 7): | 5'-AGGCTGCGGGAAGGACATCA-3' |

Primer F13F is complimentary to the non-coding stand and corresponds to nucleotides 11998 to 12017 of SEQ ID NO: 1; Primer F14 is complimentary to nucleotides 12245 to 12226 of SEQ ID NO: 1.

In addition to the two primer sets for detecting the aforementioned α-globin gene deletions, a third pair of primers was employed to amplify an unrelated region of a subject's DNA, to serve as a positive control for the amplification reaction. A 268 bp region surrounding the 5' end of the β globin gene (located on chromosome 11) was selected for amplification as the positive control, using the following primers purchased from Perkin-Elmer Cetus (Norwalk, Conn.):

| Primer GH20F (SEQ ID NO: 8): | 5'-FGAAGAGCCAAGGACAGGTAC-3' |
|---|---|
| Primer PCO4 (SEQ ID NO: 9): | 5'-CAACTTCATCCACGTTCACC-3' |

The relevant portion of the β-globin gene locus, which is known in the art, is set forth in SEQ ID NO: 10. [See GENBANK locus HUMHBB, "Human beta globin region on chromosome 11." Accessions U01317, J00179, J00093, J00094, J00096, J00158–J00175, J00177, J00178, K01239, K01890, K02544, M18047, M19067, M24868, M24886, X00423, X00424, and X00672.] The β-chain amino acid sequence is set forth in SEQ ID NO: 11. Primer GH20F is complimentary to the non-coding stand and corresponds to nucleotides 492 to 511 of SEQ ID NO: 10; Primer PCO4 is complimentary to nucleotides 759 to 740 of SEQ ID NO: 10. These primers are known to generate a 268 bp PCR product comprising ~200 bp of DNA upstream (5') of exon 1 of the hemoglobin β-chain gene and extending through most of exon 1. See Bauer et al., JAMA, 265:472–7 (1991). This segment of the β-globin genetic locus was chosen as the positive control because it is not the site of frequent deletions; it has been used in a variety of amplification techniques and applications as a control for amplification efficiency. See, e.g., Bauer et al. (1991); Dode et al. (1990), supra. The skilled artisan understands that other genetic locii that are not the site of frequent deletions also are useful controls for amplification efficiency.

The first of each pair of primers (Primer F13F, Primer F37.1F, and Primer GH20F) was labelled with fluorescein (F) at its 5' end (using fluoroscein amidite) to permit detection and analysis of PCR products obtained therefrom. (FluoroPrime™ kit, Pharmacia.) Other suitable fluorophore labels and radioisotopic labels will be apparent to those in the art.

Polymerase Chain Reaction

A Gene Amp™ PCR System 9600 thermal cycler from Perkin-Elmer Cetus (Norwalk, Conn.) was employed for all PCR amplifications. The PCR amplifications were performed with a stock (10×) PCR amplification buffer containing: 500 mM KCl, 100 mM Tris-HCl, 15 mM MgCl$_2$, and 0.1 g/L of gelatin, pH 8.3. Each 20 µL amplification reaction mixture contained PCR amplification buffer (1×), 0.2 pmol of each selected primer, 2.0 nmol dNTP's (dATP, dCTP, dGTP, and dTTP, from Pharmacia Biotechnology (Piscataway, N.J.)), DNA template (200–1600 ng), and 0.25U of recombinant Taq polymerase (Perkin-Elmer Cetus). No overlaying the reactions with oil was necessary.

The cycling sequence was as follows: (1) DNA denaturation at 94° C. for 3 minutes; (2) 35 cycles of denaturation at 94° C. for 30 seconds, annealing at 55° C. for 60 seconds, and extension at 72° C. for 60 seconds; (3) a final extension at 72° C. for 3 minutes; and (4) cooling at 4° C. Samples were held at 4° C. on the thermal cycler or in a refrigerator until analyzed as described below.

A blank amplification reaction containing all reagents but without template DNA was used as a negative control. As a positive control, each set of PCR tubes included a sample of human placental DNA (ONCOR, Gaithersburg, Md.) or known normal (αα/αα) human leukocyte DNA.

The optimal reaction conditions for multiplex polymerase chain reaction (M-PCR), in which two or all three sets of primers were employed in a single PCR reaction, were found to be the same as those described above.

Fragment Analysis and Quantitation

PCR products were analyzed using electrophoresis on a 2% agarose gel (Metaphor™, FMC BioProducts, Rockland, Me.) with TAE buffer (40 mM Tris acetate, 1 mM EDTA, pH 8.0) containing 0.5 mg/L of ethidium bromide for visualization of DNA. A 6 µL sample from a PCR reaction mixture was mixed with 2 µL of loading buffer (0.25% bromophenol blue, 0.25% xylene cyanol FF, and 40% sucrose in water) and run on agarose gel at 100 V for 45 minutes at room temperature. The gel was viewed under UV illumination and photographed.

To measure the relative amounts of M-PCR amplification products (amplicons) in a quantitative manner, the M-PCR reaction products were separated by electrophoresis on a 6% polyacrylamide gel using a DNA sequencer (ALF™, Pharmacia Biotechnology, Inc.). Electrophoretic conditions were 1500 volts and 34 watts. The gel was thermostated at 42° C. Samples (1 µL PCR reaction mixture and 1 µL stop solution (deionized formamide/Blue Dextran; Pharmacia Biotechnology)) were denatured at 94° C. for 3 min. prior to loading on the gel.

The fluorescein-labelled primers permitted quantitative detection of fluorescent, amplified PCR products from the M-PCR reactions. Fluorescence was measured using a laser power of 3 milliwatts, and fluorescence peak areas were determined by integration using fragment analysis software (Fragment Manager™, Pharmacia). The ratios of the 248 and 375 bp amplicon peak areas to the 268 bp control amplicon peak area were determined in this manner.

Fragment sizes of the M-PCR amplicons were confirmed using a 100 bp size DNA ladder (Pharmacia Biotechnology, Inc.) in one of the lanes of the sequencing gels. The DNA ladder was labeled with fluorescein by treatment with fluorescein-labeled 12-dUTP (Boehringer Mannheim Biochemicals, Indianapolis, Ind.). This was accomplished by adding 2 µL each of DNA ladder (1 µg/µL), Fill-In Buffer (200 mM Tris, pH 7.6, 500 mM KCl, 100 mM, MgSO$_4$, 40 mM MgCl$_2$, 0.5 g/L bovine serum albumin), and 1 mM fluorescein-12-dUTP to 1 µL (1U/µl) Klenow Fragment (Pharmacia) and 13 µL of distilled water. The mixture was incubated for 90 minutes at room temperature and the reaction was stopped with 2 µL of 0.4M EDTA. The labeled DNA was precipitated by adding 2.5 µL of 4M LiCl and 75 µL of pre-chilled (−20° C.) absolute ethanol and freezing for 30 minutes at −70° C. The precipitated DNA was centrifuged for 20 minutes at 1200×g, washed with cold 70% ethanol and dissolved in 50 µL TE buffer. This solution is stable for at least 6 months when stored at −70° C.

Sequencing of PCR Products

To confirm that the PCR amplified products (amplicons) were the result of the binding of the primers to the intended region, the DNA sequence of each amplicon was determined. The individual amplified products were purified from agarose gels following electrophoresis by adsorption onto glass beads (Sephaglas Band Prep Kit, Pharmacia Biotechnology, Inc.). The yield and purity of the amplicons were determined qualitatively by visually comparing the fluorescence of ethidium bromide stained bands to that of a standard DNA marker (e.g., a DNA fragment size ladder) and quantitatively by determining the ratio of absorbances at 260 nm and 280 nm of samples and standards by spectrophotometry. The DNA cycle sequencing protocol was essentially that recommended in the fmol™ DNA Sequencing System (Promega, Madison, Wis.), except for the substitution of fluorescein-labeled primers (1.0 µmol/L) for radiolabeled primers. DNA sequence determinations were performed using the ALF™ DNA Sequencer (Pharmacia Biotechnology, Inc.).

Results

In one set of PCR reaction mixtures, the primer pairs described above were employed individually (one primer pair per reaction tube) to amplify human placental template DNA (40 ng/µL, i.e., ~800 ng/reaction). PCR was performed and the reaction products analyzed as described above.

Agarose gel electrophoresis of the reaction products revealed a single prominent band for each reaction, the size of which was consistent with the amplification product predicted for a given reaction (~248 bp for primers F13F and F14; ~375 bp for primers F37.1F and F37.3; and ~268 bp for primers GH20F and PCO4).

Figure 2:
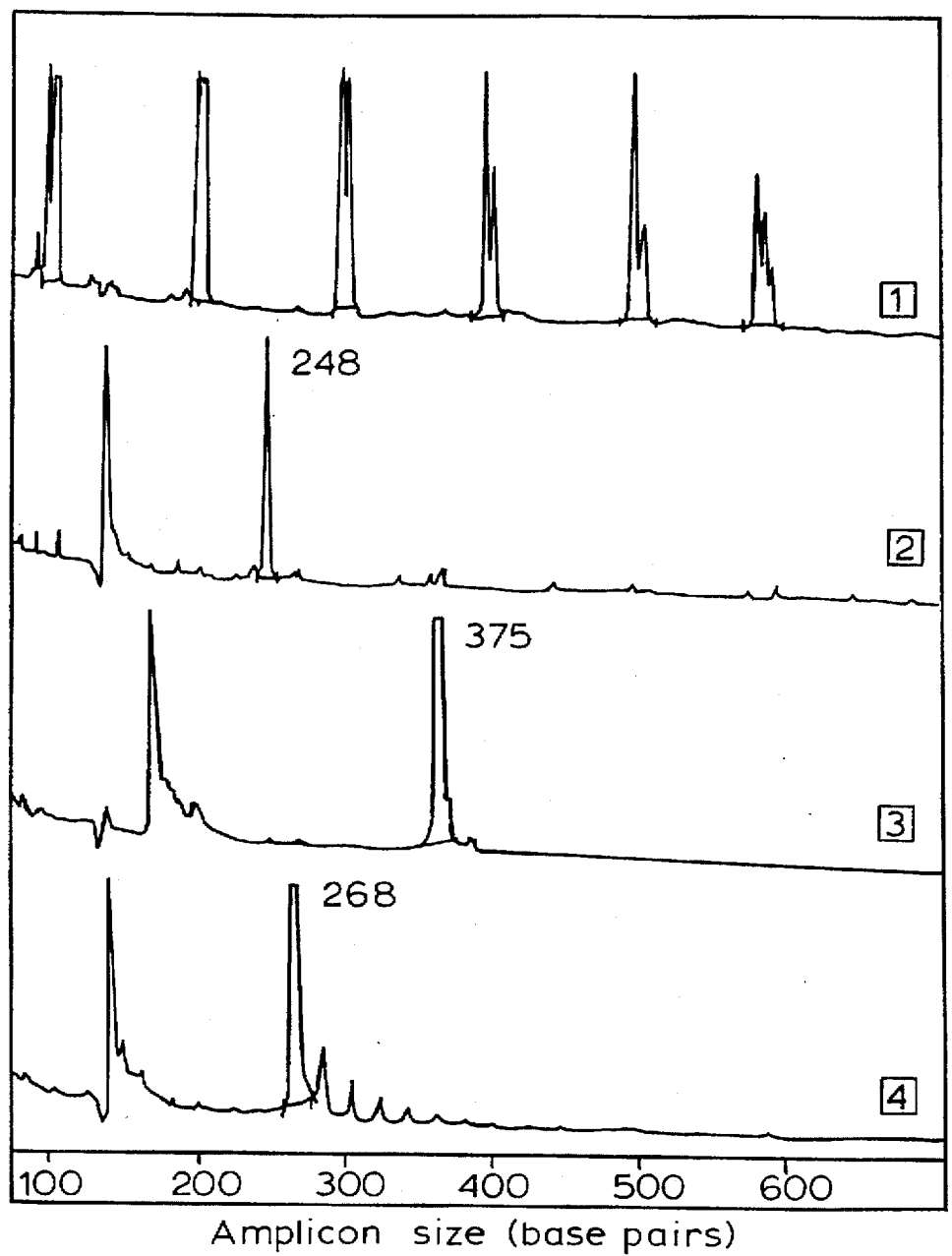
FIG. 2 graphically depicts the results of a fluorescent scan of a 6% polyacrylamide gel containing fluorescein-labelled PCR amplification products (amplicons). Fluorescence intensity (y-axis, a relative measure of the quantity of amplicons) is depeicted as a function of amplicon size (x-axis). Lane 1 (top) of the gel was loaded with a 100-bp size ladder; Lanes 2, 3, and 4 were loaded with the PCR reaction products obtained using primer pairs F13F/F14, (SEQ ID NOs: 6 and 7) F37.1F/F37.3, SEQ ID NOs: 4 and 5 and GH20F/PCO4 SEQ ID NOs: 8 and 9 (bottom), respectively, and human placental DNA as the PCR template DNA.

The identity of the PCR products was further confirmed with polyacrylamide gel electrophoresis. As depicted in FIG. 2, each reaction yielded an amplification product of the size predicted for the particular primer pair employed. Early eluting peaks (100–200 bp) represent non-specific amplification products which do not affect the quantitation of target peak areas. The identity of the amplicons also was confirmed by isolation of the individual DNA bands from the agarose gel and sequencing the DNA using a cycle sequencing protocol on the ALF™ DNA Sequencer. These results with the human placental template DNA confirmed the viability of the primers for amplification of the selected 248 bp and 375 bp regions of chromosomes 16 (the α gene locii) and the 268 bp region of chromosome 11 (the β gene locus).

Multiplex PCR reaction mixtures were prepared containing all three of the above-described primer pairs and varying concentrations of human placental template DNA (10, 20, 40, and 80 ng/µL, i.e., 200, 400, 800, and 1600 ng/reaction). PCR was performed and the reaction products analyzed as described above. Eight reactions were performed for each template concentration.

Figure 3:
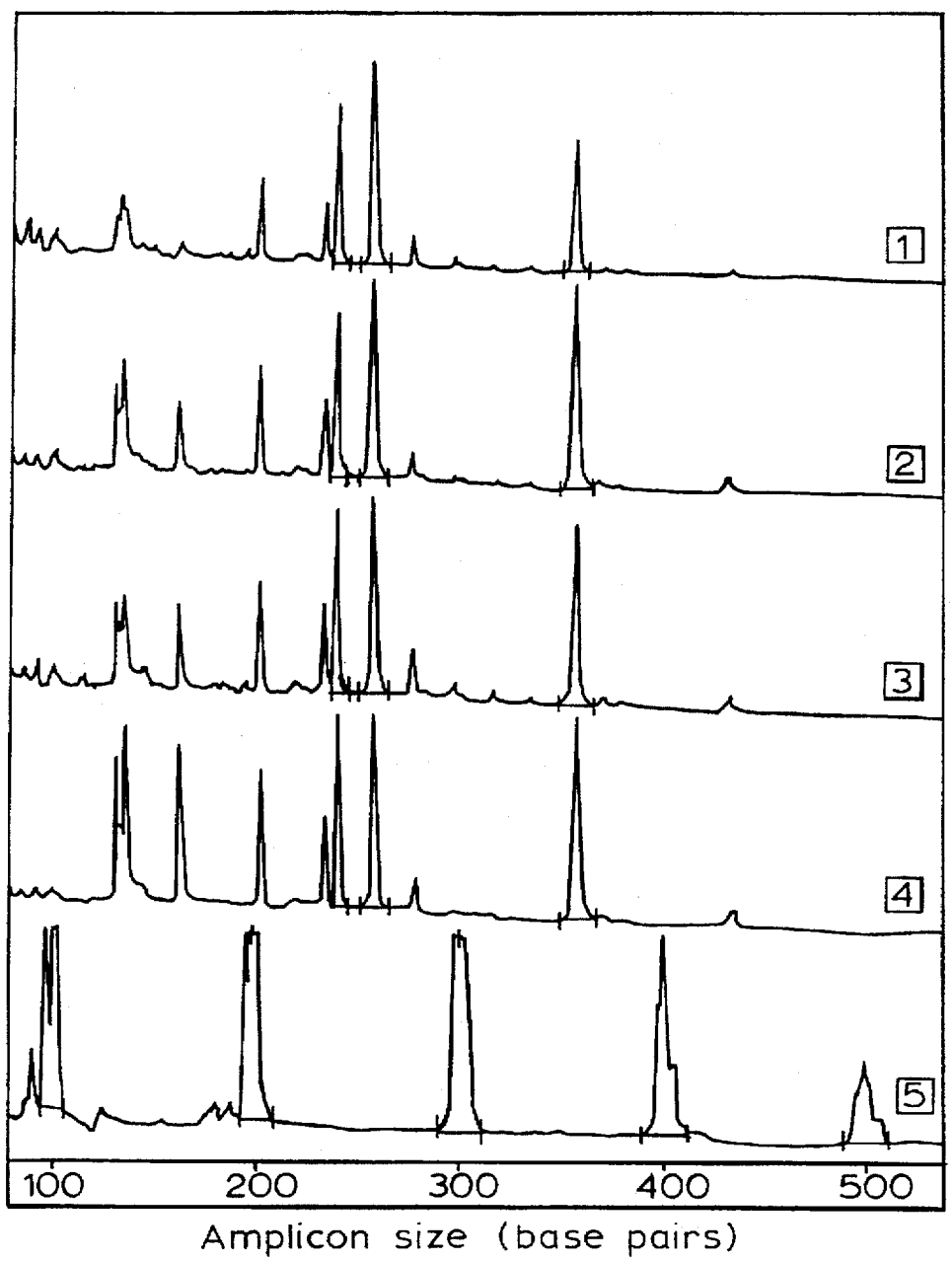
FIG. 3 graphically depicts the results of a fluorescent scan of a 6% polyacrylamide gel containing fluorescein-labelled multiplex PCR products wherein human placental DNA was employed as the template. Fluorescence intensity (y-axis, a relative measure of the quantity of amplicons) is depicted as a function of amplicon size (x-axis). Lanes 1, 2, 3, and 4 of the gel were loaded with the PCR reaction products of PCR reactions that initially contained 10, 20, 40, and 80 ng/µL of template DNA. Lane 5 was loaded with a 100-bp size ladder.

As predicted, agarose gel electrophoresis of the reaction products revealed three prominent bands of ~248 bp, ~375 bp, and ~268 bp. The samples were further analyzed on polyacrylamide gels, which permitted relative quantification of each amplicon band by measurement of the area of fluorescence peaks (FIG. 3). The ratio of α-gene deletion-sensitive amplicon peak areas (248 and 375 bp products) to the area of the control peak (268 bp product) are summarized in Table 1 (expressed as mean values for eight samples, plus or minus one standard deviation).

TABLE 1

CONCENTRATION DEPENDENCE OF PEAK AREA RATIOS

| TEMPLATE DNA CONCENTRATION (ng/µL) | 248/268 (n = 8) | PEAK AREA RATIO 375/268 (n = 8) |
|---|---|---|
| 10 | 0.79 ± 0.14 | 0.92 ± 0.27 |
| 20 | 0.68 ± 0.03 | 1.00 ± 0.03 |
| 40 | 0.65 ± 0.07 | 0.87 ± 0.08 |
| 80 | 0.60 ± 0.06 | 0.95 ± 0.05 |

The ratios of the amplified products to the control were relatively constant, but the reproducibility was deemed unacceptable (coefficient of variation greater than 10%) at initial template DNA concentrations below 20 ng/µL. The presence of the background peaks at peak sizes other than 248, 268, and 375 do not affect the quantitation of the peaks of interest, and these background peaks have not been further characterized. The reproducible peak area ratios indicated the viability of multiplex PCR with these three primer pairs.

To demonstrate the viability of the multiplex PCR procedure for detecting (α-globin gene deletions in human subjects, additional multiplex PCR reaction mixtures were prepared containing the three primer pairs and containing human leukocyte template DNA, prepared from the blood of fifteen human subjects as described above. To determine the ability of this M-PCR protocol to detect α-globin gene deletions, the genotype of each subject was also determined independently via Southern blot hybridization studies using methods known in the art. (See Sambrook et al., supra.) For example, genomic DNA from a subject is digested with the restriction endonucleases Bam HI, Eco RI, and Bgl II, electrophoresed, blotted, and probed with a radioactively-labelled probe specific for a-chain gene sequences. A preferred α-chain gene probe is ATCC clone pJW101 (ATCC Accession No. 57601, ATCC/NIH Repository Catalog of Human and Mouse DNA Probes and Libraries, Seventh Ed., (1993)). A suitable control probe is ATCC clone pBRZ (ATCC Accession No. 57599).

Figure 4:
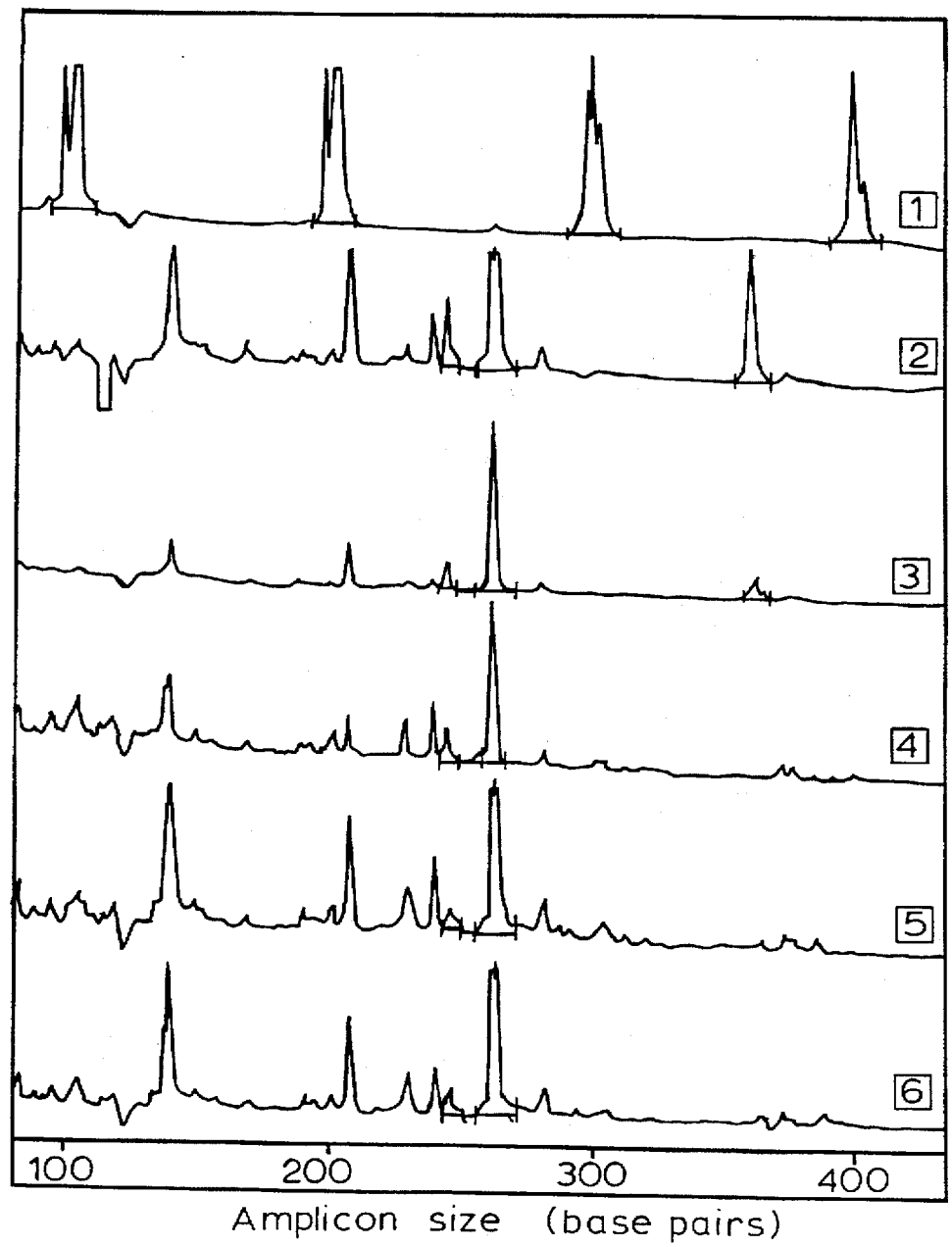
FIG. 4 graphically depicts the results of a fluorescent scan of a 6% polyacrylamide gel containing fluorescein-labelled multiplex PCR products wherein human leukocyte DNA was employed as the template. Fluorescence intensity (y-axis, a relative measure of the quantity of amplicons) is depicted as a function of amplicon size (x-axis). Lane 1 (top) was loaded with a 100 bp size ladder. Lanes 2–6 were loaded with PCR reaction products of reactions that contained template DNA from subjects of known genotypes: Lane 2, αα/αα; Lane 3, αα/–α$^{3.7}$α; Lane 4, –α$^{3.7}$α/–α$^{3.7}$α; Lane 5, –α$^{3.7}$α/--SEA; and Lane 6, –α$^{3.7}$α/--MED.

M-PCR was performed and the reaction products were analyzed on agarose and polyacrylamide gels as described above. Genotypes, peak area measurements, and peak area ratios determined for each subject are summarized in Table 2. Fluorescence scanning measurements for selected subjects are depicted in FIG. 4.

TABLE 2

CORRELATION OF GENOTYPES AND M-PCR PEAK MEASUREMENTS

| | | AREAS AND AREA RATIOS FOR AMPLIFIED PRODUCTS | | | | |
|---|---|---|---|---|---|---|
| | | Peak Area | | | Peak Area Ratio | |
| Patient Number | Genotype | 248 bp peak | 268 bp peak | 375 bp peak | 248/268 | 375/268 |
| 1 | $-\alpha^{3.7}\alpha/-\alpha^{3.7}\alpha$ | QNS* | 6096 | — | QNS | — |
| 2 | $(\alpha\alpha/\alpha\alpha)/(\zeta/\zeta\zeta)$ | 1313 | 10133 | 5032 | 0.13 | 0.50 |
| 3 | $-\alpha^{3.7}\alpha/\alpha\alpha$ | QNS | 5879 | 1093 | QNS | 0.19 |
| 4 | $(\alpha\alpha/\alpha\alpha)/(\zeta\zeta/\zeta\zeta)$ | 3901 | 13232 | 9665 | 0.29 | 0.73 |
| 5 | $\alpha\alpha/$--SEA | QNS | 2003 | 504 | QNS | 0.25 |
| 6 | $\alpha\alpha\alpha/\alpha\alpha$ | 2000 | 12265 | 6111 | 0.16 | 0.50 |
| 7 | $(\alpha\alpha/$--SEA$)/(\zeta\zeta/\zeta\zeta)$ | 457 | 10261 | 3269 | 0.04 | 0.32 |
| 8 | $-\alpha^{3.7}\alpha/-\alpha^{4.2}\alpha$ | QNS | 7719 | 1778 | QNS | 0.23 |
| 9 | $\alpha\alpha/\alpha\alpha$ | 816 | 10176 | 5319 | 0.08 | 0.52 |
| 10 | $-\alpha^{3.7}\alpha/$--SEA | 464 | 12323 | — | 0.04 | — |
| 11 | $-\alpha^{3.7}\alpha/$--MED | 334 | 12145 | — | 0.03 | — |
| 12 | $-\alpha^{4.2}\alpha/\alpha\alpha$ | 5293 | 13221 | 9820 | 0.40 | 0.74 |
| 13 | $(\alpha\alpha/$--BRIT$)/(-\zeta/\zeta\zeta)$ | 445 | 13866 | 1184 | 0.03 | 0.10 |
| 14 | $\alpha\alpha/\alpha\alpha$ | 2322 | 13561 | 9624 | 0.17 | 0.71 |
| 15 | $-\alpha^{4.2}\alpha/$--SEA | 494 | 12655 | 3222 | 0.04 | 0.25 |

*QNS, quantity not sufficient for reliable anaylsis.

The results summarized in Table 2 and FIG. 4 demonstrate the correlation between an $-\alpha^{3.7}$ deletion genotype and a reduced 375/268 peak area. For example, the 375/268 peak ratio of subject 3 (heterozygous for the $-\alpha^{3.7}$ deletion; peak ratio of 0.19) was significantly reduced compared to that of subject number 9 (normal genotype; peak ratio of 0.52). Deletions of the same locus on both of a subject's chromosomes results in the complete absence of the corresponding deletion-sensitive PCR amplicon. (See, e.g., FIG. 4, lanes 4–6.) Both the 375/268 and 248/268 ratios are reduced in subjects having a --SEA or --MEA deletion on one chromosome.

Only eleven of the fifteen samples had sufficient DNA for reliable quantitation of the 248/268 area ratios for detecting --SEA and --MED deletions. This shortcoming was attributed to the fact that the amplification efficiency of the --SEA/--MED locus is significantly lower for whole blood DNA than for purified placental DNA (FIG. 4). The peak ratios for the eleven samples were consistent with the genotypes of the samples.

The differences observed in peak heights and areas between FIGS. 3 and 4 probably reflect different amplification efficiencies between placental DNA and that of adult subjects, since all of the primers were in the M-PCR reaction at equal concentrations. Varying the relative concentration of primer pairs resulted in more even peak areas, but this also resulted in slightly poorer precision.

In a preferred embodiment for resolving all three peaks satisfactorily, the M-PCR is performed using a reaction mixture containing approximately 0.4 pmol of each primer for amplifying the 375 and 248 bp deletion-sensitive regions, and approximately 0.2 pmol of primers GH20F and PCO4 for amplifying the 268 bp control region.

The intra-run and between-run reproducibility of the ratios for Southern blot-confirmed normal and heterozygote genotypes were determined by replicate analysis. The intra-run peak ratios (mean ±standard deviation) for the 248/268 and the 375/268 ratios in normals ($\alpha\alpha/\alpha\alpha$) was 0.200±0.032 and 0.790±0.081 (n=6). The intra-run mean for the 248/268 and 375/268 ratios in $-\alpha^{3.7}$ heterozygotes were 0.201±0.025 and 0.191±0.026 (n=7). In the between-run replicate analysis (5 runs over 8 weeks at 1–2 week intervals), the 248/268 and the 375/268 ratios in normals was 0.303±0.067 and 0.879±0.163 (n=5). The between-run mean for the 248/268 and 375/268 ratios in $-\alpha^{3.7}$ heterozygotes were 0.268±0.075 and 0.217±0.059 (n=5).

The procedures described above have a number of internal controls to enhance reliability. For example, the region surrounding exon 1 of the β-globin locus is an excellent control for amplification efficiency since it is not the site of frequent deletions. Moreover, heretofore undetected mutations which might affect amplification efficiency would easily be detected by comparing amplicon ratios with those for controls included in each run. Deletions which might affect the control region only would result in increased (not decreased) ratios for both the $-\alpha^{3.7}$ and --SEA/--MED amplicons when compared to control samples.

DNA controls for the --SEA and --MED deletions were not included in each run. However, the multiplex format nonetheless provided an internal control for these deletions since each --SEA or --MED deletion also affects the $-\alpha^{3.7}$ amplicon area. Therefore, changes in the 248/268 and 375/268 ratios are in the same direction and of similar magnitude.

As shown in Table 2 (subject 13), the --BRIT deletion [see Higgs et al. (1989), supra] to the α genes locus, which reduces both the 375 bp $-\alpha^{3.7}$ and the 248 bp --SEA/--MED amplicons in much the same way as the --SEA and --MED deletions reduce these amplicon peaks, can also be detected with this M-PCR procedure. Although the primers described herein fail to distinguish between --SEA, --MED and --BRIT deletions, these conditions should be distinguishable by family history, ethnic origin, etc., if desired. It will be apparent that the teachings herein and existing knowledge of the nucleotide sequence for the α-globin gene cluster permits the selection of alternative primer pairs to the primer pairs described herein, to arrive at alternative deletion-sensitive amplicons that are specific to these α-globin gene deletions and other α-globin gene deletions. See, e.g., Example 4.

The protocol described herein is simple enough to be performed in a routine clinical laboratory. The use of M-PCR and automated fragment analysis allows at least 30–40 samples to be processed in one day, on a single polyacrylamide gel. Although we describe quantitation from a large polyacrylamide gel on the ALF™ system, the amplicons could be quantified on any conventional fluorescence densitometer capable of scanning thin acrylamide gels. Alternatively, the amplicons are quantified by automated capillary electrophoresis systems (Applied Biosystems, Foster City Calif.). It will also be apparent that the amplicons can be quantified radiometrically (i.e., by using radiolabelled primers instead of fluorophore-labelled primers).

Since the method requires only microliter quantities of a subject's blood, screening of large populations can be performed conveniently. The skilled artisan further understands that, while template DNA was purified from human blood, DNA purified from other tissues is expected to be useful as template DNA as well.

EXAMPLE 2

Use of M-PCR to Detect a Hypertensive Phenotype

The following exemplary data demonstrates that the M-PCR protocol described in Example 1 is useful for predicting a potential of a normotensive human subject for developing hypertension, and likewise is useful for determining a genetic abnormality that is pertinent to selection of the proper treatment of certain hypertensive human subjects.

DNA for use as M-PCR template DNA was isolated as described in Example 1 from whole blood samples of 132 African-Americans from whom blood specimens had been drawn for routine hematoglogical testing. These patients were defined as hypertensive if they fulfilled at least one of the following criteria: (1) diastolic blood pressure exceeding 95 mm Hg, or (2) presently undergoing physician-prescribed drug therapy for previously-diagnosed hypertension.

Multiplex PCR analysis was performed as described in Example 1 with each patient's isolated DNA, using two sets of two oligonucleotide primers simultaneously in the PCR reaction mixtures: (1) Primers F37.1F and F37.3, to amplify the 375 bp $-\alpha^{3.7}$ deletion-sensitive amplicon, and (2) Primers GH20F and PCO4, to amplify the β-globin control amplicon. The $-\alpha^{3.7}$ deletion-sensitive primer pair was selected because the $-\alpha^{3.7}$ deletion accounts for more than 95% of α-thalassemia in black Americans.

As described in Example 1, PCR reaction products were electrophoresed on agarose gels and polyacrylamide gels, and fluorescence peak areas and peak ratios were calculated. A patient's α-globin genotype was defined as "Deletion Present" (heterozygous or homozygous for an $-\alpha^{3.7}$ deletion) if the patient's 375/268 peak ratio was determined to be in the range 0–0.6; and as "Deletion Absent" if the 375/268 peak ratio was greater than 0.6. The cut-off ratio of 0.6 was selected based upon the within-run and between-run mean values for normal subjects determined in Example 1 (mean±SD of 0.79±0.081 and 0.879±0.163, respectively), the ratio 0.6 being approximately two standard deviations below the expected peak ratio for normal subjects. Table 3 summarizes the data obtained from this 132 patient sample:

TABLE 3

| Patients | Deletion Present | Deletion Absent |
|---|---|---|
| Normotensive | 22 | 32 |
| Hypertensive | 55 | 23 |
| Total | 77 | 55 |
| Hypertension Prevalence | 71.4% | 41.8% |
| Mean Age (Years) | 56.3 | 56.1 |
| Male | 34 (44.2%) | 22 (40.0%) |

The data in Table 3 demonstrates a heretofore unreported and unexpected correlation between the $-\alpha^{3.7}$ heterozygote genotype ("silent carrier" or "mild α-thalassemia" genotype) and hypertension in an adult patient population. More particularly, no significant statistical differences existed in the average age or in the distribution of males and females between the 77 patients identified as possessing an $-\alpha^{3.7}$ genotype and the 55 patients identified as normal. However, the difference in prevalence of hypertension between the two populations was statistically significant (p<0.001). Most of the 77 individuals identified as "deletion present" were heterozygous for the $-\alpha^{3.7}$ deletion (e.g., $-\alpha^{3.7}\alpha/\alpha\alpha$). However, hypertension appears to correlate with homozygous individuals ($-\alpha^{3.7}\alpha/-\alpha^{3.7}\alpha$) at least as strongly as with heterozygotes.

The high frequency of "Deletion Present" patients relative to the total number of reported patients in Table 4 (77/132) is not believed to reflect any bias in the patient population. Rather, the data reflects the fact that, for over 200 patients diagnosed as "Deletion Absent" using the M-PCR assay, the medical records of only 55 of them were examined to determine whether the patient was hypertensive or normotensive.

The foregoing data indicates persons having an α-globin gene mutation, and more particularly having an $-\alpha^{3.7}$ genotype that is common amongst black Americans, are significantly more likely to suffer from hypertension as adults than persons having a normal genotype at this locus. The data further demonstrates that the M-PCR protocol described in Example 1 is useful for determining a person's α-globin genotype. Therefore, it follows that the M-PCR protocol is useful for predicting a normotensive person's potential for developing hypertension based on the person's α-globin genotype, since an α-globin deletion genotype correlates with an increased potential for hypertension relative to a normal genotype. Likewise, the M-PCR method is useful for determining the existence of an α-globin genetic abnormality (mutation) in a hypertensive person, the presence or absence of the α-globin genetic abnormality being pertinent to a physician's prescription of the proper hypertension treatment regimen.

EXAMPLE 3

Detection of $-\alpha^{4.2}$ α-globin gene deletions with multiplex PCR

The following procedure was performed to demonstrate the utility of the M-PCR protocol described in Example 1 for screening an individual for the presence of an $-\alpha^{4.2}$ (leftward) α-globin gene deletion. While the prevalence of this genotype is low in the general population, its prevalence can be as high as 58% in some Chinese populations.

DNA for use as M-PCR template DNA was isolated from the blood of two human subjects as described in Example 1.

Using Southern hybridization analysis, the first patient's α-globin genotype was confirmed to be normal, and the second patient was confirmed to be an $-\alpha^{4.2}\alpha/\alpha\alpha$ heterozygote.

Two primers were selected and synthesized as described in Example 1 to amplify a 416 bp region that is absent in a chromosome 16 harboring an $-\alpha^{4.2}$, --SEA, or --MED deletion (see FIG. 1):

| | |
|---|---|
| Primer F42.2F (SEQ ID NO: 12): | 5'-FGGGATTACAGCGTGAGCCAA-3' |
| Primer F42.3 (SEQ ID NO: 13): | 5'-GAGGAAGGAAGGGGTGGACT-3' |

Primer F42.2F is complimentary to the non-coding strand and corresponds to nucleotides 5290 to 5309 of SEQ ID NO: 1. Primer F42.3 is complimentary to nucleotides 5705 to 5686 of SEQ ID NO: 1. Primer F42.2F was fluorescein-labelled at its 5' end as described in Example 1.

M-PCR reactions were conducted as described in Example 1 using the primer pair described immediately above and the positive control primer pair described in Example 1 for amplifying a 268 bp region surrounding the 5' end of the β-globin gene. Reaction products were analyzed on agarose and polyacrylamide gels as previously described. The 416/268 peak area ratio was significantly reduced in the M-PCR reaction products derived from the heterozygote template DNA, confirming that the M-PCR method described herein is useful for detecting an $-\alpha^{4.2}$ deletion.

To confirm within-run reproducibility, seven M-PCR reactions were conducted simultaneously for each individual. The 416/268 peak area ratios (±standard deviation) were determined to be 0.910 (±0.054) for the normal subject and 0.294 (±0.025) for the $-\alpha^{4.2}$ heterozygote subject.

To confirm between-run reproducibility, five separate M-PCR reactions were conducted over a six-week period. The 416/268 peak area ratios (±standard deviation) were determined to be 0.945 (±0.061) for the normal subject and 0.231 (±0.048) for the $-\alpha^{4.2}$ heterozygote subject.

The significant difference observed in peak ratios between normal and heterozygote individuals demonstrates that the M-PCR method described herein is useful for detecting the presence of $-\alpha^{4.2}$ deletion mutations in a human subject's genome.

From the preceding three examples, it will be apparent that the M-PCR methods described herein can be employed to detect the presence of the major α-gene deletions that afflict populations throughout the world, including the $-\alpha^{3.7}$, $-\alpha^{4.2}$, --SEA, --MED, and other deletions.

EXAMPLE 4

Use of M-PCR to Detect an Increased Potential for Developing a Blood-Related Disorder The following example is conducted to demonstrate that the M-PCR protocol described in the preceding examples is useful for predicting a potential of a human subject for developing a blood-related disorder, and likewise is useful for determining a genetic abnormality that is pertinent to selection of the proper treatment of certain human subjects afflicted with the blood-related disorder. Such blood-related disorders include hypertension, stroke, myocardial infarction, hemochromatosis, preeclampsia/eclampsia conditions, thalassemic disorders, diabetes, and other blood-related disorders.

DNA for use as M-PCR template DNA is isolated as described in Example 1 from whole blood samples of human subjects. It is contemplated that any purified genomic DNA from the subject is similarly suitable for use as template DNA, other tissue sources and purification methods being known in the art. In one embodiment, the human subjects are healthy human subjects who are monitored by qualified medical practitioners to determine whether the subjects subsequently develop the blood-related disorder(s) of interest. In an alternative embodiment, the human subject population includes subjects that are known to be afflicted with the blood-related disorder(s), or known to have been afflicted with the blood-related disorder(s) of interest, based upon medical examination of the subject or upon examination of the subject's medical history.

Multiplex PCR analysis is performed as described in Example 1 with each subject's isolated DNA, using two or more pairs of oligonucleotide primers simultaneously in the PCR reaction mixtures: (1) at least one pair of α-globin gene deletion-sensitive primers to amplify at least one deletion-sensitive amplicon (i.e., primer pairs described in the preceding examples or primer pairs selected and synthesized according to the teachings herein; and (2) a pair of primers (e.g., Primers GH20F and PCO4) to amplify a control amplicon. For each individual pair of primers, the quantity of each primer in the M-PCR reaction mixture preferably is the same and is in the range of 0.2 to 0.4 pmol/primer. In a preferred embodiment, primer pairs for amplifying deletion-sensitive amplicons are present at about 0.4 pmol (of each primer) quantities, whereas about 0.2 pmol of each of the primers for amplifying the β-globin control amplicon are employed. In a preferred embodiment, the multiplex PCR analysis also is performed using template DNA from one or more confirmed normal ((αα/αα) subjects, to permit a determination of a control (normal subject) amplicon peak area ratio for the particular PCR reagents and reaction conditions. Similarly, multiplex PCR may be performed simultaneously using template DNA from subjects who are confirmed (e.g., by DNA sequencing or Southern hybridization analysis) to be heterozygous for a particular α-gene deletion, to establish an expected amplicon peak area ratio for the particular heterozygote genotype.

PCR reaction products are electrophoresed on agarose gels and polyacrylamide gels, and fluorescence peak areas and peak area ratios are calculated. A subject's α-globin genotype is defined based upon the peak area ratio of deletion-sensitive amplicons to control amplicons. Subjects are classified by their defined genotypes.

Routine statistical analysis is performed to demonstrate that the M-PCR results predict an increased potential of a human subject for developing a blood-related disorder. More particularly, the human subjects are monitored to determine whether the subjects previously have developed and/or subsequently develop the blood-related disorder(s) of interest. For any particular disorder, a greater prevalence of the disorder amongst individuals with an α-globin deletion genotype versus a normal genotype suggests that individuals having the deletion genotype are more likely to develop the disorder than normal individuals. This suggestion is confirmed by routine statistical analysis, e.g., at an attained level of significance of 0.05 (p<0.05). Prior to performing the statistical analysis, the human subjects preferably are further classified by age, sex, and/or other characteristics that a medical practitioner familiar with the blood-related disorder of interest understands to influence an individual's likelihood of developing the disorder. In this manner, the potential confounding role of such factors in the statistical analysis is eliminated. For each α-globin deletion genotype that predicts an increased potential of developing a particular blood-related disorder, subjects determined to have that particular genotype may be advised with respect to the increased potential for developing the disorder. Such genetic counseling permits a subject to make the most appropriate medical and lifestyle management choices prospectively.

Additional data obtained from a population of non-hospitalized individuals confirms that an increased risk exists for development of hypertension in older individuals with an α-globin deletion genotype (age>50 years: odds ratio 1.06, n=62 individuals; age>60: odds ratio 1.21, n=33) when compared to individuals of the same age group without an α-globin deletion genotype. See Armitage & Berry, *Statistical Methods in Medical Research*, 3rd Ed., London: Blackwell Scientific Publications (1994) (describing calculation of odds ratios).

Moreover, preliminary data obtained from the same group of non-hospitalized individuals demonstrated that an increased risk exists for the development of acute myocardial infarction in older individuals with an α-globin deletion genotype (age>50: odds ratio 1.07, n=62; age>60: odds ratio 1.17, n=33) when compared to a similar control group of normal individuals. Also, an association was found to exist between an α-globin deletion genotype and diabetes which is manifest in a group of 153 non-hospitalized individuals from the same geographic area as the two groups above. The odds ratio for diabetes when the α-globin deletion genotype is present versus when it is absent was determined to be 2.04.

While the present invention has been described in terms of specific embodiments, it is understood that variations and modifications will occur to those skilled in the art. Accordingly, only such limitations as appear in the appended claims should be placed on the invention.

What is claimed is:

1. A method of screening a human subject for an increased risk of developing a blood-related disorder, comprising the steps of:
   (a) assaying genomic DNA of a human subject to determine a presence or an absence of an α-globin deletion mutation; and
   (b) screening for an increased risk of developing a blood-related disorder from the presence or absence of an α-globin deletion mutation in said genomic DNA, wherein the presence of an α-globin deletion mutation in the genomic DNA correlates with an increased risk of developing a blood-related disorder, and wherein said blood-related disorder is selected from the group consisting of hypertension, myocardial infarction, and diabetes.

2. The method of claim 1 wherein the human subject is normotensive and the blood-related disorder is hypertension.

3. The method of claim 2 wherein the α-globin deletion mutation is selected from the group consisting of an $-\alpha^{3.7}$ deletion, an MED deletion, an --SEA deletion, an $-\alpha^{4.2}$ deletion, and an --BRIT deletion.

4. The method of claim 2 wherein the genomic DNA is assayed to determine the presence or the absence of an $-\alpha^{3.7}$ deletion mutation.

5. The method of claim 4 wherein the human subject is heterozygous for an $-\alpha^{3.7}$ deletion.

6. The method of claim 1 wherein said human subject has a genotype free of β-globin mutations that cause deficient synthesis of normal β-globin chains.

7. A method of screening for an increased potential for developing hypertension in a normotensive human individual comprising the steps of:
   (a) isolating DNA from said human individual;
   (b) assaying said DNA for the presence of a deletion relative to DNA of a normal human subject, said deletion comprising a reduction in the number of α-globin genes in the genome of the normotensive human individual; and
   (c) screening for an increased potential for developing hypertension in said normotensive human individual, wherein the presence of said deletion in the DNA isolated from the normotensive human individual is indicative of an increased potential for developing hypertension.

8. The method of claim 7 wherein the deletion is present in the DNA of the normotensive human individual.

9. The method of claim 7 wherein in step (b) said deletion is a deletion of at least 3.7 kilobases of DNA.

10. The method of claim 7 wherein the deletion is selected from the group consisting of an $-\alpha^{3.7}$ deletion, an --MED deletion, an --SEA deletion, an $-\alpha^{4.2}$ deletion, and an --BRIT deletion.

11. The method of claim 7 wherein step (b) comprises assaying said DNA for the presence of an $-\alpha^{3.7}$ deletion relative to DNA of a normal human subject.

12. The method of claim 7 wherein step (b) comprises at least one of:
   (i) determining a partial nucleotide sequence of the DNA from said human individual, said partial nucleotide sequence indicating the presence or absence of said deletion;
   (ii) performing a restriction endonuclease digestion of the DNA from said human individual and a Southern hybridization, said Southern hybridization indicating the presence or absence of said deletion; and
   (iii) performing a multiplex polymerase chain reaction with the DNA from said human individual to determine the presence or absence of said deletion.

13. The method of claim 7 wherein step (b) comprises performing a multiplex polymerase chain reaction with the DNA from said human individual to determine the presence or absence of said deletion.

14. The method of claim 7 wherein said human individual has a genotype free of β-globin mutations that cause deficient synthesis of normal β-globin chains.

15. A method for determining an increased potential for developing hypertension in a human individual comprising the steps of:
   (a) isolating genomic DNA from said human individual;
   (b) performing a multiplex polymerase chain reaction with said genomic DNA to amplify a marker portion and a control portion thereof, wherein the presence of an α-globin gene deletion in said genomic DNA reduces the quantity of marker amplicons produced in the multiplex polymerase chain reaction relative to the quantity of control amplicons produced in said multiplex polymerase chain reaction; and (c) determining a potential for developing hypertension from the quantity of marker amplicons relative to the quantity of control amplicons.

16. The method of claim 15 wherein step (c) further comprises the steps of:

(i) determining a ratio of marker amplicons to control amplicons produced in the multiplex polymerase chain reaction; and (ii) comparing the ratio of step (i) to a ratio of marker amplicons to control amplicons produced in a multiplex polymerase chain reaction performed with genomic DNA of a normal human subject, wherein a lower marker amplicon to control amplicon ratio of step (i) indicates an increased potential for developing hypertension.

17. The method of claim 15 wherein step (b) further comprises the step of preparing a polymerase chain reaction solution, said solution comprising genomic DNA isolated from said human individual, a first pair of oligonucleotide primers for amplifying said marker portion of said DNA, and a second pair of oligonucleotide primers for amplifying said control portion of said DNA.

18. The method of claim 17 wherein said first pair of primers consists of a primer having the nucleotide sequence of SEQ ID NO: 4 and a primer having the nucleotide sequence of SEQ ID NO: 5.

19. The method of claim 18 wherein said second pair of primers consists of a primer having the nucleotide sequence of SEQ ID NO: 8 and a primer having the nucleotide sequence of SEQ ID NO: 9.

20. The method of claim 19 wherein in step (c) a marker amplicon to control amplicon ratio that is less than or equal to 0.6 is correlated with an increased potential for developing hypertension.

21. The method of claim 16 further comprising:

isolating genomic DNA from a normal human being;

performing a control multiplex polymerase chain reaction with the genomic DNA of the normal human being to amplify a marker portion and a control portion thereof; and determining a ratio of marker amplicons to control amplicons produced in the control multiplex polymerase chain reaction;

wherein in step (ii), a lower marker amplicon to control amplicon ratio for the human individual compared to the ratio of marker amplicons to control amplicons for the normal human being indicates an increased potential for developing hypertension.

22. The method of claim 15 wherein said human individual has a genotype free of β-globin mutations that cause deficient synthesis of normal β-globin chains.

23. A method of determining an increased potential for developing a blood-related disorder, comprising the steps of:

(a) isolating genomic DNA from a human individual;

(b) assaying said DNA for a deletion relative to DNA of a normal human subject, said deletion reducing the number of α-globin genes in the genome of the human individual; and (c) determining an increased potential for developing a blood-related disorder in said human individual, wherein the presence of said deletion in the genomic DNA of the human individual is indicative of an increased potential for developing said blood-related disorder, said blood-related disorder selected from the group consisting of hypertension, myocardial infarction, and diabetes.

24. The method of claim 23 wherein said human individual has a genotype free of β-globin mutations that cause deficient synthesis of normal β-globin chains.

25. A kit comprising:

an assay means for assaying genomic DNA from a human subject for the presence of an α-globin deletion mutation; and a means for correlating the presence of an α-globin deletion mutation to an increased potential of developing a blood-related disorder, said disorder selected from the group consisting of hypertension, myocardial infarction, and diabetes.

26. The kit of claim 25 wherein the assay means comprises a pair of α-globin deletion-sensitive oligonucleotide primers.

27. The kit of claim 26 wherein the assay means further comprises first and second samples of human genomic DNA, said first sample having a homozygous normal α-globin genotype, said second sample having a heterozygous αα/α-globin-deletion genotype.

28. The kit of claim 27 wherein the second sample of human genomic DNA has a heterozygous αα/–$\alpha^{3.7}$α genotype.

29. An assay for identifying a mild α-thalassemia deletion genotype in a human individual comprising the steps of:

(a) providing genomic DNA from said human individual;

(b) performing a multiplex polymerase chain reaction with said genomic DNA to amplify a marker portion and a control portion thereof, wherein the presence of an α-globin gene deletion in said genomic DNA reduces the quantity of marker amplicons produced in the multiplex polymerase chain reaction relative to the quantity of control amplicons produced in said multiplex polymerase chain reaction;

(c) determining a ratio of marker amplicons to control amplicons produced in the multiplex polymerase chain reaction;

(d) comparing the ratio of step (c) to a ratio of marker amplicons to control amplicons produced in a multiplex polymerase chain reaction performed with genomic DNA of a normal human subject; and (e) identifying a mild α-thalassemia deletion genotype in said human individual from said ratio of step (c), wherein a mild α-thalassemia genotype in said individual correlates with a lower marker amplicon to control amplicon ratio of step (c) compared to the ratio of marker amplicons to control amplicons produced in a multiplex polymerase chain reaction performed with genomic DNA of a normal human subject.

30. An assay according to claim 29 for identifying an $-\alpha^{3.7}\alpha/\alpha\alpha$ genotype in a human individual, wherein said marker portion of genomic DNA comprises a portion of chromosome 16 located between the α2 and α1 gene loci, and wherein in step (b), the presence of an $-\alpha^{3.7}/\alpha\alpha$ genotype in said genomic DNA reduces the quantity of marker amplicons produced in the multiplex polymerase chain reaction relative to the quantity of control amplicons produced in said multiplex polymerase chain reaction.

31. An assay according to claim 29 for identifying an $-\alpha^{4.2}\alpha/\alpha\alpha$ genotype in a human individual, wherein said marker portion of genomic DNA comprises a portion of chromosome 16 located 5' to the α2 gene locus, and wherein in step (b), the presence of an $-\alpha^{4.2}/\alpha\alpha$ genotype in said genomic DNA reduces the quantity of marker amplicons produced in the multiplex polymerase chain reaction relative to the quantity of control amplicons produced in said multiplex polymerase chain reaction.

32. An assay according to claim 29 wherein the marker amplicon to control amplicon ratio of step (c) is greater than zero.

33. The assay of claim 29 wherein in step (e) a mild α-thalassemia deletion genotype is identified from a marker amplicon to control amplicon ratio of step (c) that is at least two standard deviations below the ratio of marker amplicons to control amplicons produced in multiplex polymerase chain reactions performed with genomic DNA of normal human subjects.

34. A method of determining a hypertension-correlated genetic disorder in a hypertensive human individual comprising the steps of:

(a) isolating DNA from said human individual;

(b) assaying said DNA for a deletion relative to DNA of a normal human subject, said deletion comprising a reduction in the number of α-globin genes in the genome of the hypertensive human individual; and (c) determining a presence of a hypertension-correlated genetic disorder in said individual from a presence of said deletion in said DNA.

35. A kit for determining the α-globin genotype of a human individual comprising, in association:

a first pair of oligonucleotide primers for amplifying a first marker portion of a human chromosome 16, said first marker portion being absent from a human chromosome 16 having a single α-gene deletion selected from the group consisting of an $-\alpha^{3.7}$ deletion and an $-\alpha^{4.2}$ deletion;

a second pair of oligonucleotide primers for amplifying a second marker portion of a human chromosome 16, said second marker portion being present in a human chromosome 16 having the single α-gene deletion and being absent from a human chromosome 16 having an --MED deletion; and a control pair of oligonucleotide primers for amplifying a control portion of human genomic DNA, wherein said first pair of oligonucleotide primers consists of a primer having the nucleotide sequence of SEQ ID NO: 4 and a primer having the nucleotide sequence of SEQ ID NO: 5; and wherein said second pair of oligonucleotide primers consists of a primer having the nucleotide sequence of SEQ ID NO: 6 and a primer having the nucleotide sequence of SEQ ID NO: 7.

36. A kit for determining the α-globin genotype of a human individual comprising, in association:

a first pair of oligonucleotide primers for amplifying a first marker portion of a human chromosome 16, said first marker portion being absent from a human chromosome 16 having an $-\alpha^{3.7}$ deletion;

a second pair of oligonucleotide primers for amplifying a second marker portion of a human chromosome 16, said second marker portion being present in a human chromosome 16 having the single α-gene deletion and being absent from a human chromosome 16 having an --MED deletion;

a third pair of oligonucleotide primers for amplifying a third marker portion of a human chromosome 16, said third marker portion being absent from a human chromosome 16 having an $-\alpha^{4.2}$ deletion; and a control pair of oligonucleotide primers for amplifying a control portion of human genomic DNA, wherein said first pair of oligonucleotide primers consists of a primer having the nucleotide sequence of SEQ ID NO: 4 and a primer having the nucleotide sequence of SEQ ID NO: 5; wherein said second pair of oligonucleotide primers consists of a primer having the nucleotide sequence of SEQ ID NO: 6 and a primer having the nucleotide sequence of SEQ ID NO: 7; and wherein said third pair of oligonucleotide primers consists of a primer having the nucleotide sequence of SEQ ID NO: 12 and a primer having the nucleotide sequence of SEQ ID NO: 13.

37. A kit for determining the α-globin genotype of a human individual by multiplex polymerase chain reaction with genomic DNA of said individual, said kit comprising, in association:

a first pair of oligonucleotide primers for amplifying a first marker portion of a human chromosome 16, said first marker portion being absent from a human chromosome 16 having an $-\alpha^{3.7}$ deletion wherein said first pair of oligonucleotide primers consists of a primer having the nucleotide sequence of SEQUENCE ID NO: 4 and a primer having the nucleotide sequence of SEQUENCE ID NO: 5;

a second pair of oligonucleotide primers for amplifying a second marker portion of a human chromosome 16, said second marker portion being present in a human chromosome 16 having a single α-gene deletion selected from the group consisting of an $-\alpha^{3.7}$ deletion and an $-\alpha^{4.2}$ deletion and being absent from a human chromosome 16 having an --MED deletion;

a third pair of oligonucleotide primers for amplifying a third marker portion of a human chromosome 16, said third marker portion being absent from a human chromosome 16 having an $-\alpha^{4.2}$ deletion wherein said third pair of oligonucleotide primers consists of a primer having the nucleotide sequence of SEQUENCE ID NO: 12 and a primer having the nucleotide sequence of SEQUENCE ID NO: 13; and a control pair of oligonucleotide primers for amplifying a control portion of human genomic DNA, said primer pairs permitting a determination, via multiplex polymerase chain reaction, of a $-\alpha^{3.7}\alpha/\alpha\alpha$ mild α-thalassemia genotype, a $-\alpha^{4.2}\alpha/\alpha\alpha$ mild α-thalassemia genotype, and α-thalassemia trait genotypes wherein at least two α-globin gene alleles have been deleted.

38. A kit according to claim 37 wherein said second pair of oligonucleotide primers consists of a primer having the nucleotide sequence of SEQ ID NO: 6 and a primer having the nucleotide sequence of SEQ ID NO: 7.

39. A kit according to claim 38 wherein said control pair of oligonucleotide primers consists of a primer having the nucleotide sequence of SEQ ID NO: 8 and a primer having the nucleotide sequence of SEQ ID NO: 9.

* * * * *